(12) United States Patent
Furuta et al.

(10) Patent No.: US 11,382,912 B2
(45) Date of Patent: Jul. 12, 2022

(54) CONTROLLED-RELEASE PREPARATION

(71) Applicant: NIPPON SHINYAKU CO., LTD., Kyoto (JP)

(72) Inventors: Shouji Furuta, Kyoto (JP); Naoto Hattori, Kyoto (JP)

(73) Assignee: NIPPON SHINYAKU CO., LTD., Kyoto (JP)

( * ) Notice: Subject to any disclaimer, the term of this patent is extended or adjusted under 35 U.S.C. 154(b) by 260 days.

(21) Appl. No.: 16/763,574

(22) PCT Filed: Nov. 15, 2018

(86) PCT No.: PCT/JP2018/042359
§ 371 (c)(1),
(2) Date: May 13, 2020

(87) PCT Pub. No.: WO2019/098300
PCT Pub. Date: May 23, 2019

(65) Prior Publication Data
US 2020/0360373 A1 Nov. 19, 2020

(30) Foreign Application Priority Data

Nov. 16, 2017 (JP) .............................. JP2017-220777

(51) Int. Cl.
*A61K 31/4965* (2006.01)
*A61K 9/20* (2006.01)

(52) U.S. Cl.
CPC ........ *A61K 31/4965* (2013.01); *A61K 9/2009* (2013.01); *A61K 9/2013* (2013.01); *A61K 9/2027* (2013.01); *A61K 9/2054* (2013.01); *A61K 9/2059* (2013.01)

(58) Field of Classification Search
CPC .............. A61K 31/4965; A61K 9/2009; A61K 9/2013; A61K 9/2027; A61K 9/2054; A61K 9/2059
See application file for complete search history.

(56) References Cited

U.S. PATENT DOCUMENTS

| | | |
|---|---|---|
| 6,656,502 B1 | 12/2003 | Hara et al. |
| 2004/0102436 A1 | 5/2004 | Asaki et al. |
| 2006/0204569 A1 | 9/2006 | Obae et al. |
| 2011/0015211 A1 | 1/2011 | Murakami et al. |
| 2011/0105518 A1 | 5/2011 | Kuwano |
| 2011/0118254 A1 | 5/2011 | Kyoi |
| 2011/0178103 A1 | 7/2011 | Matsuda et al. |
| 2012/0101276 A1 | 4/2012 | Itou et al. |
| 2012/0316177 A1 | 12/2012 | Hirasawa et al. |
| 2014/0221397 A1 | 8/2014 | Murakami et al. |
| 2018/0333413 A1 | 11/2018 | Furuta et al. |

FOREIGN PATENT DOCUMENTS

| | | | | |
|---|---|---|---|---|
| CN | 107811994 A | * | 3/2018 | ......... A61K 31/4965 |
| EP | 1 645 568 A1 | | 4/2006 | |
| JP | S62-120315 A | | 6/1987 | |
| JP | S63-215620 A | | 9/1988 | |
| JP | 2009-506070 A | | 2/2009 | |
| JP | 2014-009208 A | | 1/2014 | |
| WO | 1998/041210 A1 | | 9/1998 | |
| WO | 2002/088084 A1 | | 11/2002 | |
| WO | 2005/005484 A1 | | 1/2005 | |
| WO | 2007/025182 A2 | | 3/2007 | |
| WO | 2009/107736 A1 | | 9/2009 | |
| WO | 2009/154246 A1 | | 12/2009 | |
| WO | 2009/157396 A1 | | 12/2009 | |
| WO | 2009/157397 A1 | | 12/2009 | |
| WO | 2009/157398 A1 | | 12/2009 | |
| WO | 2010/150865 A1 | | 12/2010 | |
| WO | 2011/099573 A1 | | 8/2011 | |
| WO | 2017/029594 A1 | | 2/2017 | |
| WO | 2017/042731 A1 | | 3/2017 | |
| WO | 2017/098998 A1 | | 6/2017 | |
| WO | 2017/121806 A1 | | 7/2017 | |

OTHER PUBLICATIONS

Tatsuya Atsumi et al., "Improvement of skin temperature of fingers by beraprost sodium in patients with Raynaud's phenomenon," Japanese Journal of Clinical Immunology, vol. 16, Issue 5, pp. 409-414, 1993.
David B. Badesch et al., "Longterm Survival Among Patients with Scleroderma-associated Pulmonary Arterial Hypertension Treated with Intravenous Epoprostenol," The Journal of Rheumatology, vol. 36, No. 10, pp. 2244-2249, 2009, [online] <www.jrheum.org>, retrieved Mar. 11, 2020.
G. Bergman et al., "Prostacyclin: Haemodynamic and Metabolic Effects in Patients With Coronary Artery Disease," The Lancet. vol. 317, Issue 8220, pp. 569-572, Mar. 14, 1981, Elsevier B.V.
Yan Chen et al., "Protective effect of beraprost sodium, a stable prostacyclin analog, in the development of cigarette smoke extract-induced emphysema," The American Journal of Physiology—Lung Cellular and Molecular Physiology, vol. 296, L648-L656, 2009, [online] <journals.physiology.org/journal/ajplung>, retrieved Mar. 11, 2020.
P. Henriksson et al., "Prostacyclin infusion in patients with acute myocardial infarction," British Heart Journal, vol. 53, No. 2, pp. 173-179, 1985, [online] <https://heart.bmj.com/>, retrieved Mar. 12, 2020.
Tetsuya Hirano et al., "Effect of Beraprost Sodium (TRK-100) on Erythrocyte Deformability, Blood Viscosity and Thrombus Formation in Rats," Japanese Journal of Thrombosis and Hemostasis, vol. 1, Issue 2, pp. 94-105, 1990.

(Continued)

*Primary Examiner* — Alicia L Otton

(57) ABSTRACT

An object of the present invention is to provide a controlled-release preparation containing 2-{4-[N-(5,6-diphenylpyrazin-2-yl)-N-isopropylamino]butyloxy}-N-(methylsulfonyl)acetamide as an active ingredient and having an excellent release property. Another object of the present invention is to provide a controlled-release preparation characterized by containing 2-{4-[N-(5,6-diphenylpyrazin-2-yl)-N-isopropylamino]butyloxy}-N-(methylsulfonyl)acetamide, a water-soluble polymer, a functional starch, and an alkaline substance, and having a pH of 10 or more.

19 Claims, 5 Drawing Sheets

(56) References Cited

OTHER PUBLICATIONS

Marco IDZKO et al., "Inhaled iloprost suppresses the cardinal features of asthma via inhibition of airway dendritic cell function," The Journal of Clinical Investigation, Vo. 117, No. 2, pp. 464-472, Feb. 2007, American Society for Clinical Investigation.

T. Matsumoto et al., "The efficacy of oral beraprost sodium, a prostaglandin I2 analogue, for treating intermittent claudication in patients with arteriosclerosis obliterans," International Angiology, vol. 29, Suppl. 1 to No. 2, pp. 49-54, 2010, Edizioni Minerva Medica.

S. Nishio et al., "[Pharmacological and clinical properties of beraprost sodium, orally active prostacyclin analogue]," Nihon Yakurigaku Zasshi (Folia Pharmacologica Japonica), vol. 117, Issue 2, pp. 123-130, Feb. 2001.

Teruhiko Umetsu et al., "Antithrombotic Effect of TRK-100, a Novel, Stable PGI2 Analogue," Japanese Journal of Pharmacology, vol. 43, Issue 1, pp. 81-90, 1987.

Uptravi® Tablets 0.2mg • 0.4mg, Pharmaceutical Interview Forms, revised on Nov. 2016 (2nd edition); and Partial English Translation thereof.

Masateru Yamada et al., "Amelioration by beraprost sodium, a prostacyclin analogue, of established renal dysfunction in rat glomerulonephritis model," European Journal of Pharmacology, vol. 449, pp. 167-176, 2002, Elsevier B.V.

Hao Yin et al., "Prostaglandin I2 and E2 mediate the protective effects of cyclooxygenase-2 in a mouse model of immune-mediated liver injury," Hepatology, vol. 45, No. 1, pp. 159-169, Jan. 2007.

European Patent Office, "Extended European Search Report," issued in European Patent Application No. 18 878 215.5, which is a counterpart to U.S. Appl. No. 16/763,574, dated Jul. 16, 2021, 16 pages.

Irene M. Lang and Sean P. Gaine, "Recent advances in targeting the prostacyclin pathway in pulmonary arterial hypertension," European Respiratory Review, vol. 24, pp. 630-641, 2015.

European Medicines Agency, "Assessment Report, Uptravi, International non-proprietary name: selexipag, Procedure No. EMEA/H/C/003774/0000," 117 pages, Apr. 1, 2016.

* cited by examiner

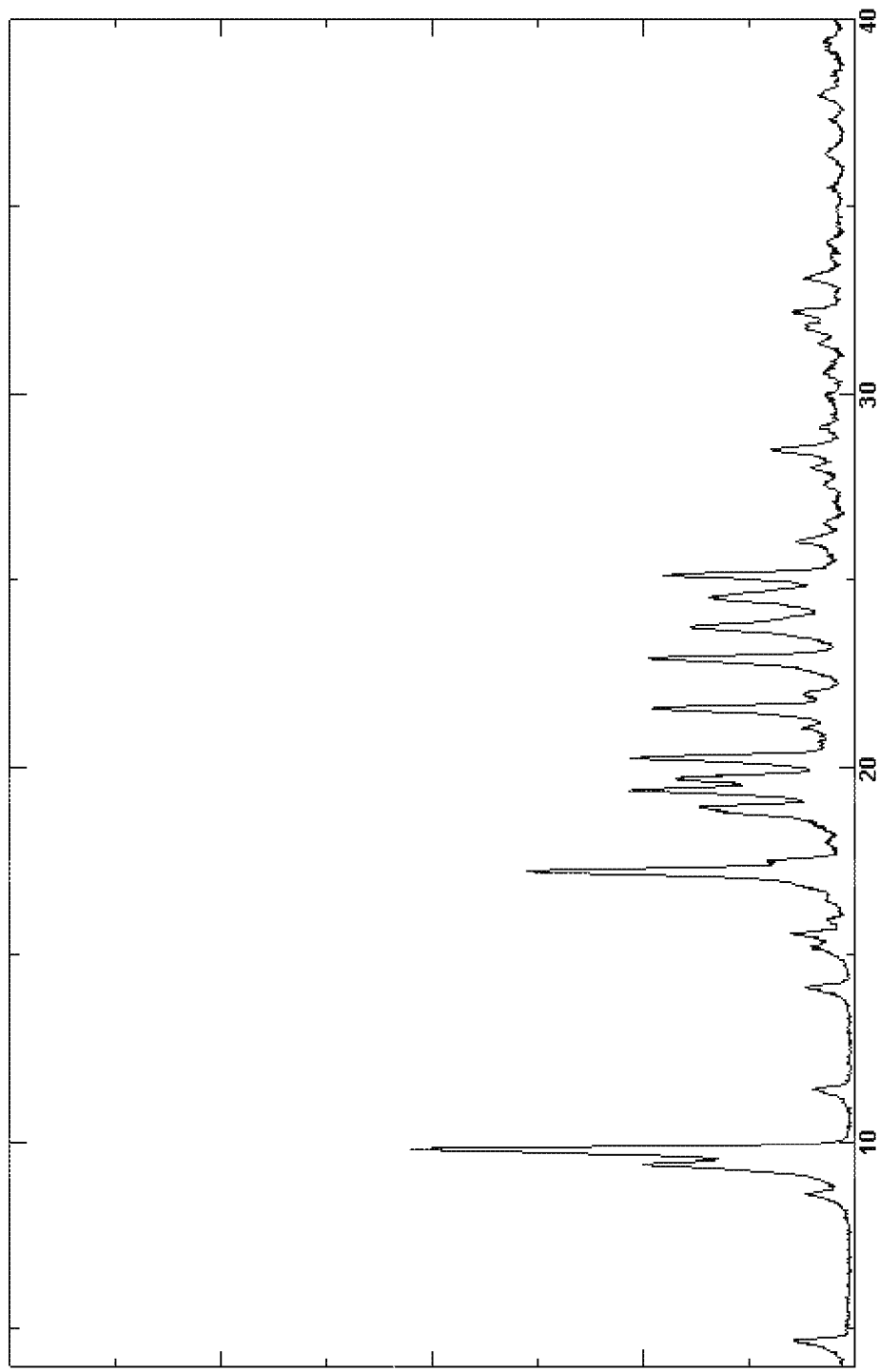
[FIG. 1]

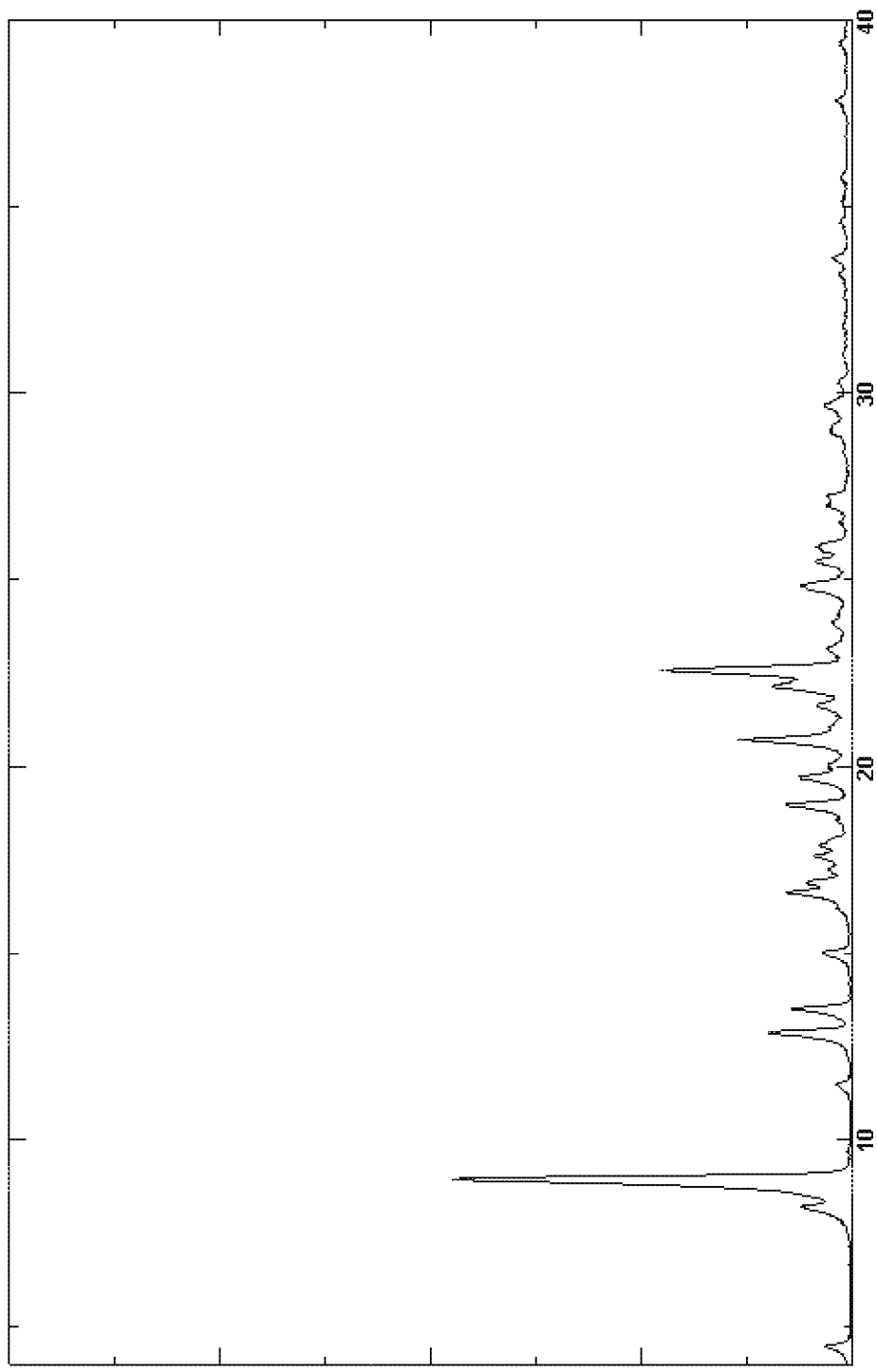
[FIG. 2]

[FIG. 3]
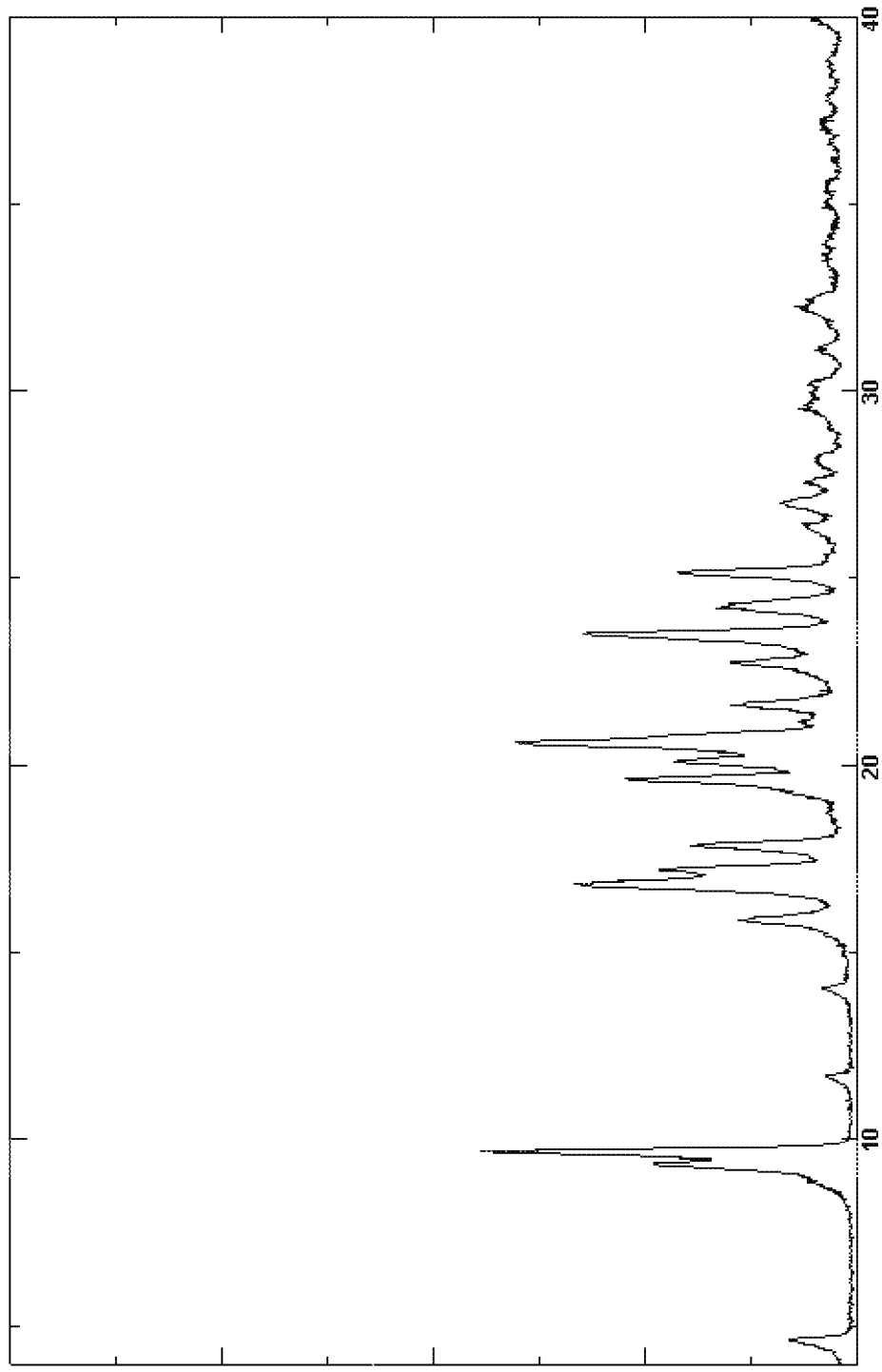

[FIG. 4]
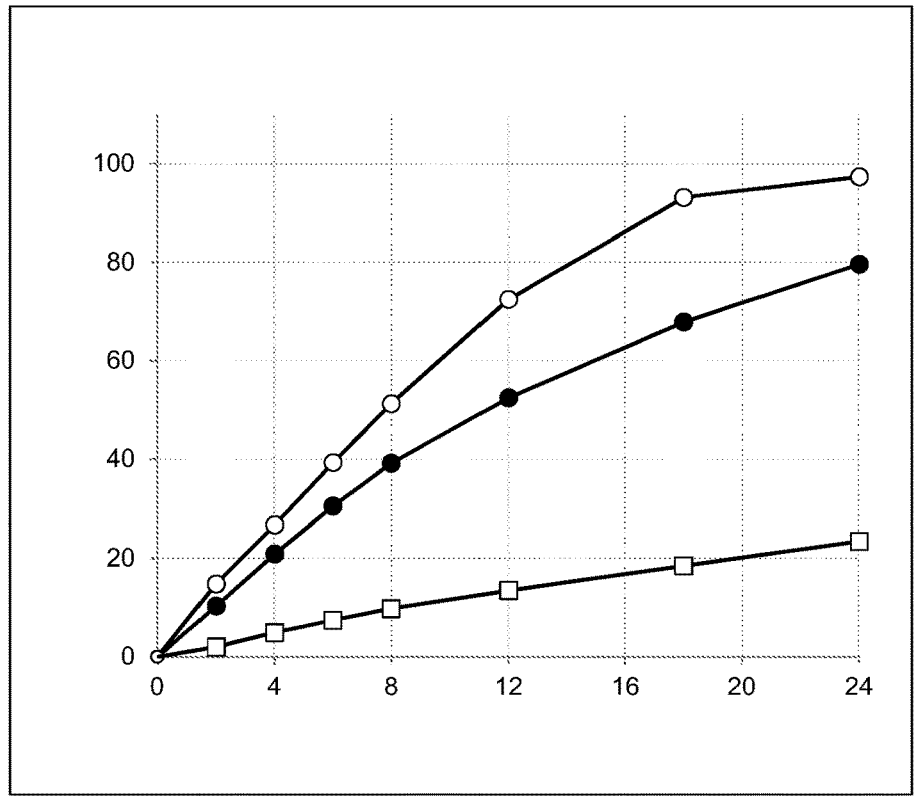
[FIG. 5]
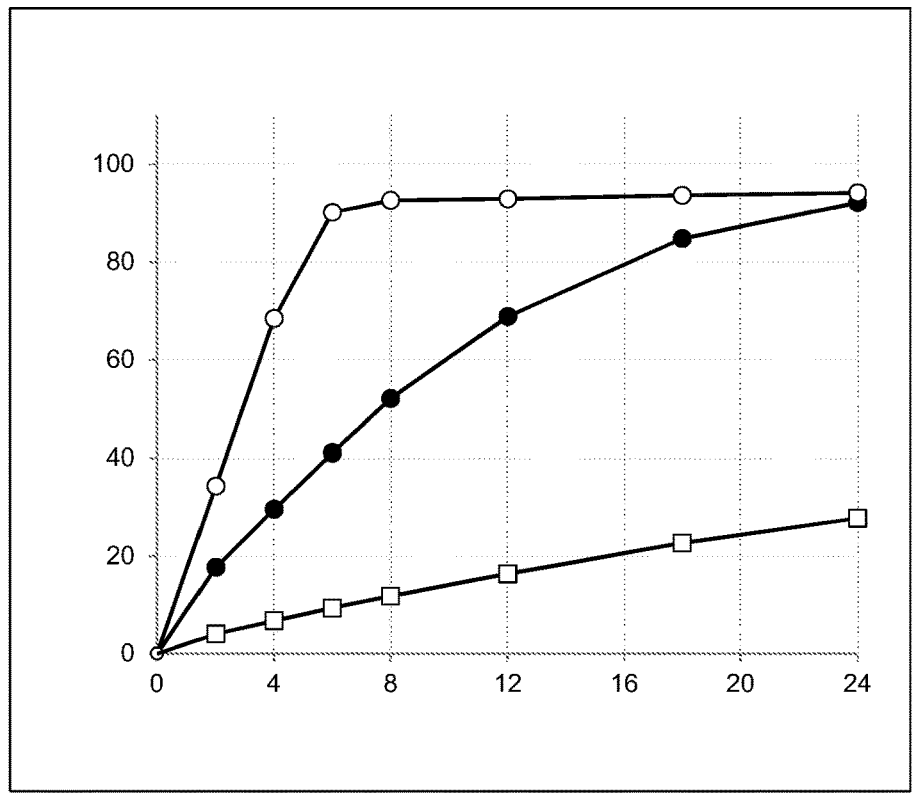

[FIG. 6]
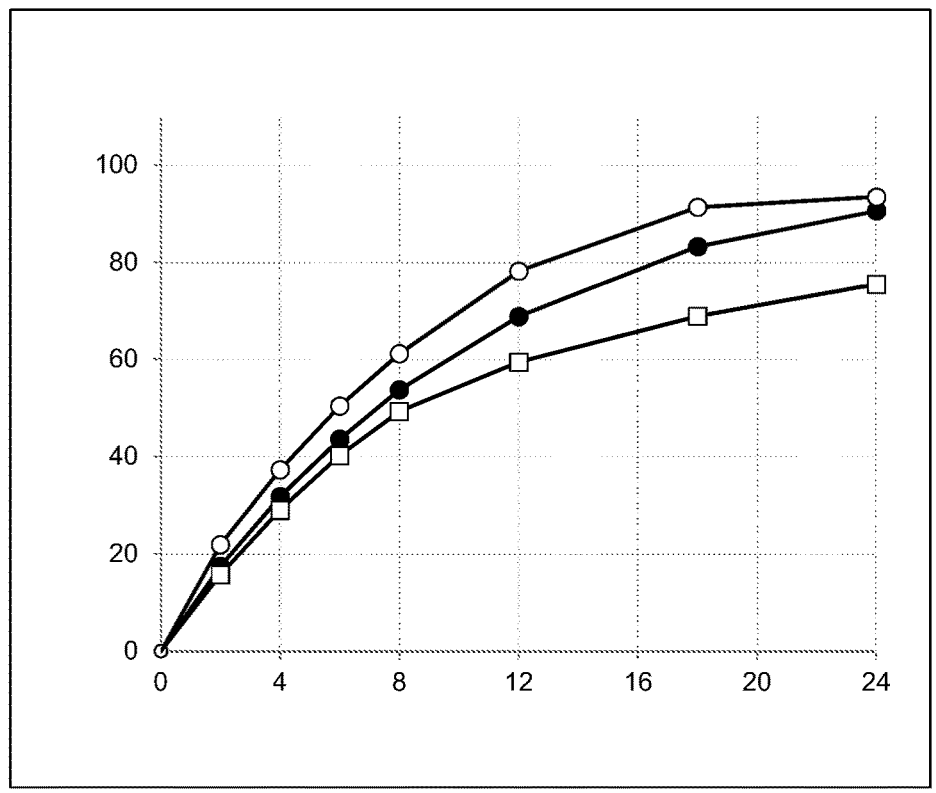
[FIG. 7]
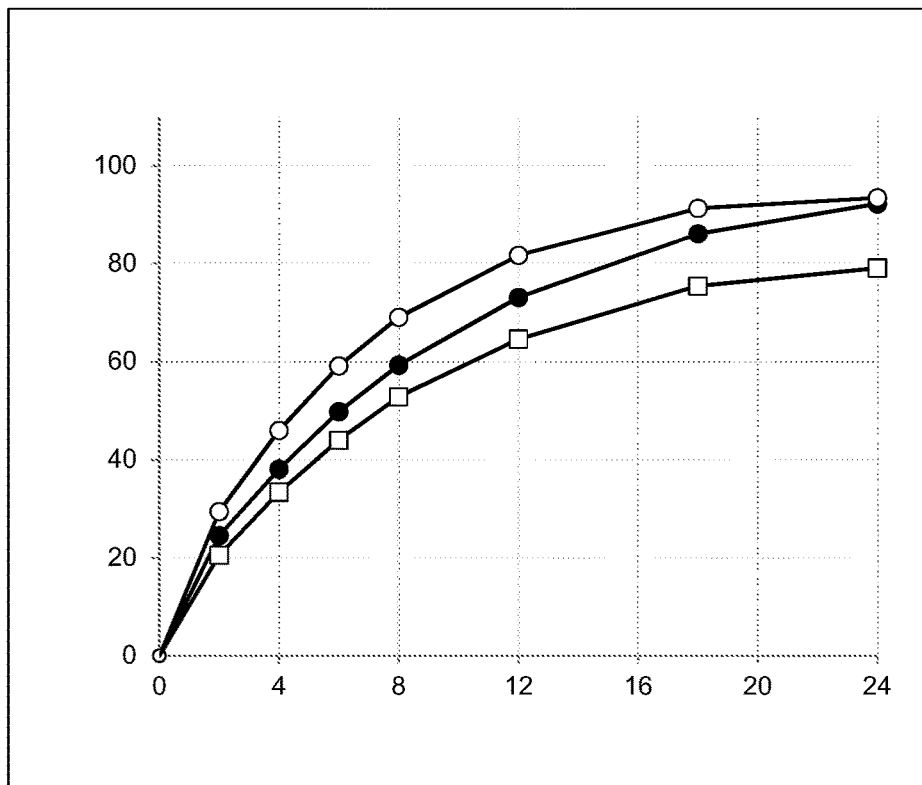

CONTROLLED-RELEASE PREPARATION

CROSS REFERENCE TO RELATED APPLICATIONS

This patent application is a U.S. national stage application under 35 U.S.C. § 371 of International Patent Application No. PCT/JP2018/042359 filed on Nov. 15, 2018, which claims the benefit of foreign priority to Japanese Patent Application No. JP 2017-220777 filed on Nov. 16, 2017. The International Application was published in Japanese on May 23, 2019, as International Publication No. WO 2019/098300 A1 under PCT Article 21(2).

TECHNICAL FIELD

The present invention relates to a controlled-release preparation containing 2-{4-[N-(5,6-diphenylpyrazin-2-yl)-N-isopropylamino]butyloxy}-N-(methylsulfonyl)acetamide (hereinafter referred to as "Compound A") as an active ingredient.

[Chem. 1]

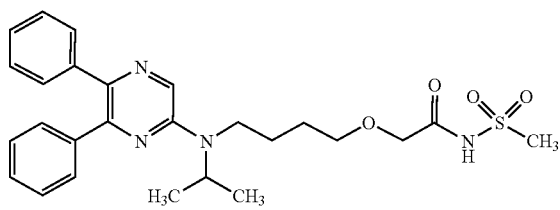

BACKGROUND ART

A sustained-release preparation can gradually release a drug, and therefore can maintain a blood concentration of the drug over a long period of time. A sustained-release preparation has advantages such as duration of drug efficacy due to sustained-release of the drug, a reduction in adverse effects due to prevention of sudden rise of the blood concentration of the drug, a reduction in troublesome medication and prevention of medication failure due to a decrease in administration frequency, and improvement of medication compliance, and therefore, recently, the development of sustained-release preparations has been advanced for many drugs.

The sustained-release preparation is one of the controlled-release preparations, and the release property of a drug can be controlled by, for example, mixing the drug in a base in a matrix. However, among such preparations, some preparations are destroyed themselves by the peristaltic movement of the gastrointestinal tract and the drug dissolves faster than an expected time.

In general, as the sustained-release preparation, a hydrogel preparation using a water-soluble polymer as a sustained-release base has been known (see, for example, PTL 1 to PTL 5). Further, a sustained-release preparation using a functional starch has also been known (see, for example, PTL 6).

However, there has been no report of a sustained-release preparation containing a water-soluble polymer, a functional starch, and an alkaline substance.

On the other hand, Compound A is known to have an excellent prostaglandin 12 (hereinafter referred to as "PGI$_2$") receptor agonistic effect and show various medicinal effects such as a platelet aggregation inhibitory effect, a vasodilating effect, a bronchial smooth muscle dilating effect, a lipid deposition inhibitory effect, and a leukocyte activation inhibitory effect (see, for example, PTL 7 to PTL 12). At present, a preparation containing Compound A as an active ingredient is used as a therapeutic agent for pulmonary arterial hypertension in the form of a normal tablet (PTL 19).

CITATION LIST

Patent Literature

[PTL 1] JP-T-2009-506070
[PTL 2] WO 2011/099573
[PTL 3] JP-A-63-215620
[PTL 4] JP-A-62-120315
[PTL 5] WO 1998/041210
[PTL 6] WO 2005/005484
[PTL 7] WO 2002/088084
[PTL 8] WO 2009/157396
[PTL 9] WO 2009/107736
[PTL 10] WO 2009/154246
[PTL 11] WO 2009/157397
[PTL 12] WO 2009/157398
[PTL 13] US 2014/0221397
[PTL 14] US 2011/0178103
[PTL 15] US 2011/0015211
[PTL 16] US 2011/0118254
[PTL 17] US 2011/0105518
[PTL 18] WO 2010/150865
[PTL 19] WO 2017/098998

Non Patent Literature

[NPL 1] Uptravi Tablets 0.2 mg, Uptravi Tablets 0.4 mg, Pharmaceutical Interview Form revised on November 2016 ($2^{nd}$ edition)
[NPL 2] Hepatology, 2007, Vol. 45, No. 1, pp. 159-169
[NPL 3] PubMed: Nihon Yakurigaku Zasshi, 2001, February, 117(2), pp. 123-130, Abstract
[NPL 4] International Angiology, 29, Suppl. 1 to No. 2, pp. 49-54, 2010
[NPL 5] Japanese Journal of Clinical Immunology, Vol. 16, No. 5, pp. 409-414, 1993
[NPL 6] Japanese Journal of Thrombosis and Hemostasis, Vol. 1, No. 2, pp. 94-105, 1990, Abstract
[NPL 7] The Journal of Rheumatology, Vol. 36, No. 10, pp. 2244-2249, 2009
[NPL 8] The Japanese Journal of Pharmacology, Vol. 43, No. 1, pp. 81-90, 1987
[NPL 9] British Heart Journal, Vol. 53, No. 2, pp. 173-179, 1985
[NPL 10] The Lancet, 1, 4880, pt 1, pp. 569-572, 1981
[NPL 11] European Journal of Pharmacology, 449, pp. 167-176, 2002
[NPL 12] The Journal of Clinical Investigation, 117, pp. 464-72, 2007
[NPL 13] American Journal of Physiology Lung Cellular and Molecular Physiology, 296: L648-L656, 2009

SUMMARY OF INVENTION

Technical Problem

The solubility of Compound A is known to depend on pH (see, for example NPL 1).

In a sustained-release preparation which is required to maintain the release of the active ingredient at a constant rate for a long period of time, it is demanded that rapid release of the drug in the gastrointestinal tract when it is orally administered be avoided, and also constant release of the drug be maintained independently of pH.

Therefore, an object of the present invention is to provide a controlled-release preparation containing Compound A as an active ingredient and capable of avoiding rapid release of Compound A and of releasing Compound A in a pH-independent manner.

Solution to Problem

As a result of intensive studies for achieving the above object, the present inventors found that there is a problem in a pharmaceutical preparation containing Compound A as an active ingredient that the controlled release of Compound A is variable due to change of pH in a digestive tract caused by enterokinesis, pH variation depending on the site of gastrointestinal tract, individual difference in pH of digestive fluid or pH change of gastrointestinal tract caused by a food and a drug. The inventors have also found that by using a water-soluble polymer, a functional starch, and an alkaline substance in a controlled-release preparation containing Compound A as an active ingredient, the release property thereof is less affected by the property of a test solution (pH) and a stirring intensity (paddle rotation speed), and thus have completed the present invention.

That is, the present invention relates to a controlled-release preparation according to any one of the following [1] to [14] (hereinafter also referred to as "controlled-release preparation of the present invention"). Also, the present invention relates to a use of the controlled-release preparation according to the following [15] and a method for treatment or prevention of a disease using the controlled-release preparation according to the following [16].

[1] A controlled-release preparation, characterized by comprising Compound A, a water-soluble polymer, a functional starch, and an alkaline substance, and having a pH of 10 or more;

[2] the controlled-release preparation according to the above [1], wherein the water-soluble polymer is a polymer whose aqueous solution at a concentration of 10 wt % or less has a viscosity of 1000 mPa·s or more at 25° C.;

[3] the controlled-release preparation according to the above [1] or [2], wherein the water-soluble polymer is at least one selected from the group consisting of hypromellose, hydroxypropylcellulose, and polyvinyl alcohol;

[4] the controlled-release preparation according to any one of the above [1] to [3], wherein the amount of the water-soluble polymer contained in the preparation is within the range from 5 wt % to 70 wt % with respect to the total weight of the preparation;

[5] the controlled-release preparation according to any one of the above [1] to [4], wherein the functional starch is (a) or (b):

(a) a starch whose aqueous suspension at 7 wt % has a viscosity within the range from 100 mPa·s to 1500 mPa·s at 25° C.; or (b) a starch which does not disintegrate even after 1 hour in a disintegration test using an auxiliary disk according to the Japanese Pharmacopoeia 17th edition when the starch is subjected to compression molding;

[6] the controlled-release preparation according to any one of the above [1] to [5], wherein the amount of the functional starch contained in the preparation is within the range from 15 wt % to 70 wt % with respect to the total weight of the preparation;

[7] the controlled-release preparation according to any one of the above [1] to [6], wherein the total amount of the water-soluble polymer and the functional starch contained in the preparation is within the range from 25 wt % to 85 wt % with respect to the total weight of the preparation;

[8] the controlled-release preparation according to any one of the above [1] to [7], wherein the alkaline substance is an alkaline substance whose aqueous solution at 0.1 wt % has a pH of 10 or more;

[9] the controlled-release preparation according to any one of the above [1] to [8], wherein the amount of the alkaline substance contained in the preparation is within the range from 1 wt % to 15 wt % with respect to the total weight of the preparation;

[10] the controlled-release preparation according to any one of the above [1] to [9], characterized in that the preparation satisfies all the following Criteria (x) to (z):

Criterion (x): under the conditions of a dissolution test in which 900 mL of a test solution at pH 6.8 is used and a paddle rotation speed is set to 200 rpm, a dissolution rate ($R_{(x)}$) at the time t is within the range of R±15%;

Criterion (y): under the conditions of a dissolution test in which 900 mL of a test solution at pH 5.0 is used and a paddle rotation speed is set to 50 rpm, a dissolution rate ($R_{(y)}$) at the time t is within the range of R±15%; and Criterion (z): under the conditions of a dissolution test in which 500 mL of a test solution at pH 1.2 is used and a paddle rotation speed is set to 200 rpm, the preparation does not disintegrate at the time t;

wherein t is the time to release 40 to 60% of Compound A in the preparation and R is the dissolution rate at the time t, under the conditions of a dissolution test in which 900 mL of a test solution at pH 6.8 is used and the paddle rotation speed is set to 50 rpm;

[11] the controlled-release preparation according to any one of the above [1] to [10], wherein the controlled-release preparation is a sustained-release preparation;

[12] the controlled-release preparation according to any one of the above [1] to [11], wherein the controlled-release preparation is a tablet or a capsule;

[13] the controlled-release preparation according to any one of the above [1] to [12] for use in the treatment of symptoms associated with diabetic neuropathy, diabetic gangrene, a peripheral circulatory disturbance, chronic arterial occlusion, intermittent claudication, scleroderma, thrombosis, pulmonary hypertension, myocardial infarction, angina pectoris, glomerulonephritis, diabetic nephropathy, chronic renal failure, bronchial asthma, interstitial pneumonia, pulmonary fibrosis, a chronic obstructive pulmonary disease, tubulointerstitial nephritis, an inflammatory bowel disease, or spinal canal stenosis;

[14] A controlled-release preparation comprising 2-{4-[N-(5,6-diphenylpyrazin-2-yl)-N-isopropylamino]butyloxy}-N-(methylsulfonyl)acetamide as an active ingredient characterized in that the preparation satisfies all the following Criteria (x) to (z):

Criterion (x): under the conditions of a dissolution test in which 900 mL of a test solution at pH 6.8 is used and a paddle rotation speed is set to 200 rpm, a dissolution rate (R(x)) at the time t is within the range of R±15%;

Criterion (y): under the conditions of a dissolution test in which 900 mL of a test solution at pH 5.0 is used and a paddle rotation speed is set to 50 rpm, a dissolution rate (R(y)) at the time t is within a range of R±15%; and Criterion (z): under the conditions of a dissolution test in which 500 mL of a test solution at pH 1.2 is used and a paddle rotation speed is set to 200 rpm, the preparation does not disintegrate at the time t;

wherein t is the time to release 40 to 60% of 2-{4-[N-(5,6-diphenylpyrazin-2-yl)-N-isopropylamino]butyloxy}-N-(methylsulfonyl)acetamide in the preparation and R is the dissolution rate at the time t, under the conditions of a dissolution test in which 900 mL of a test solution at pH 6.8 is used and the paddle rotation speed is set to 50 rpm;

[15] Use of a controlled-release preparation in the manufacture of a medicament, wherein the preparation comprises 2-{4-[N-(5,6-diphenylpyrazin-2-yl)-N-isopropylamino]butyloxy}-N-(methylsulfonyl)acetamide, a water-soluble polymer, a functional starch and an alkaline substance and has a pH of 10 or more; and [16] A method for the treatment or prevention of a disease comprising administering a therapeutically effective amount of a controlled-release preparation to a patient in need thereof, wherein the preparation comprises 2-{4-[N-(5,6-diphenylpyrazin-2-yl)-N-isopropylamino]butyloxy}-N-(methylsulfonyl)acetamide, a water-soluble polymer, a functional starch and an alkaline substance, and has a pH of 10 or more.

BRIEF DESCRIPTION OF DRAWINGS

FIG. 1 shows a powder X-ray diffraction spectrum chart of a Form-I crystal of Compound A. The vertical axis represents a peak intensity (cps) and the horizontal axis represents a diffraction angle (2θ [°]).

FIG. 2 shows a powder X-ray diffraction spectrum chart of a Form-II crystal of Compound A. The vertical axis represents a peak intensity (cps) and the horizontal axis represents a diffraction angle (2θ [°]).

FIG. 3 shows a powder X-ray diffraction spectrum chart of a Form-III crystal of Compound A. The vertical axis represents a peak intensity (cps) and the horizontal axis represents a diffraction angle (2θ [°]).

FIG. 4 shows a dissolution profile of a tablet described in Comparative Example 2-1. The vertical axis represents a dissolution rate of Compound A (%) and the horizontal axis represents a time (hours). Black circle: dissolution rate of Compound A when a test solution at pH 6.8 was used and a paddle rotation speed was set to 50 rpm; white circle: dissolution rate of Compound A when a test solution at pH 6.8 was used and a paddle rotation speed was set to 200 rpm; and white rectangle: dissolution rate of Compound A when a test solution at pH 5.0 was used and a paddle rotation speed was set to 50 rpm.

FIG. 5 shows a dissolution profile of a tablet described in Comparative Example 2-2. The vertical axis represents a dissolution rate of Compound A (%) and the horizontal axis represents time (hours). Black circle: dissolution rate of Compound A when a test solution at pH 6.8 was used and a paddle rotation speed was set to 50 rpm; white circle: dissolution rate of Compound A when a test solution at pH 6.8 was used and a paddle rotation speed was set to 200 rpm; and white rectangle: dissolution rate of Compound A when a test solution at pH 5.0 was used and a paddle rotation speed was set to 50 rpm.

FIG. 6 shows a dissolution profile of a tablet described in Example 2-1. The vertical axis represents a dissolution rate of Compound A (%) and the horizontal axis represents a time (hours). Black circle: dissolution rate of Compound A when a test solution at pH 6.8 was used and a paddle rotation speed was set to 50 rpm; white circle: dissolution rate of Compound A when a test solution at pH 6.8 was used and a paddle rotation speed was set to 200 rpm; and white rectangle: dissolution rate of Compound A when a test solution at pH 5.0 was used and a paddle rotation speed was set to 50 rpm.

FIG. 7 shows a dissolution profile of a tablet described in Example 2-2. The vertical axis represents a dissolution rate of Compound A (%) and the horizontal axis represents a time (hours). Black circle: dissolution rate of Compound A when a test solution at pH 6.8 was used and a paddle rotation speed was set to 50 rpm; white circle: dissolution rate of Compound A when a test solution at pH 6.8 was used and a paddle rotation speed was set to 200 rpm; and white rectangle: dissolution rate of Compound A when a test solution at pH 5.0 was used and a paddle rotation speed was set to 50 rpm.

DESCRIPTION OF EMBODIMENTS

The present invention relates to a controlled-release preparation, characterized by containing Compound A, a water-soluble polymer, a functional starch, and an alkaline substance, and having a pH of 10 or more. Hereinafter, the present invention will be described in detail.

(A) Compound A

Compound A which is the active ingredient of the controlled-release preparation of the present invention is a known compound described in, for example, PTL 7 and PTL 18, and can be easily obtained by a person skilled in the art according to the method described in these patent literatures.

In the controlled-release preparation of the present invention, Compound A may be an optical isomer, a pharmaceutically acceptable salt, an amorphous form (see WO2017/029594, WO2017/042731, WO2018/015975, etc.) or a crystal form thereof, or a mixture thereof, especially a crystal form of Compound A.

Examples of such crystal form of Compound A in the controlled-release preparation of the present invention include Form-I crystal, Form-II crystal and Form-III crystal of Compound A, as well as Form-IV to -IX crystals of Compound A (see WO2017/040872, WO2018/022704, WO2018/015974, etc.).

Particularly, Form-I, Form-II and Form-III crystals of Compound A, as listed below, are preferred, and Form-I crystal of Compound A is more preferable.

Compound A is known to have, for example, the following three crystal forms (see, for example, PTL 18).

(1) A Form-I crystal of Compound A, for which a powder X-ray diffraction diagram is obtained using a Cu-Kα radiation (λ=1.54 Å), and which shows diffraction peaks at the following diffraction angles (2θ): 9.4°, 9.8°, 17.2°, and 19.4° in the powder X-ray diffraction spectrum of Compound A.

(2) A Form-II crystal of Compound A, for which a powder X-ray diffraction diagram is obtained using a Cu-Kα radiation (λ=1.54 Å), and which shows diffraction peaks at the following diffraction angles (2θ): 9.0°, 12.9°, 20.7°, and 22.6° in the powder X-ray diffraction spectrum of Compound A.

(3) A Form-III crystal of Compound A, for which a powder X-ray diffraction diagram is obtained using a Cu-Kα radiation (λ=1.54 Å), and which shows diffraction peaks at the following diffraction angles (2θ): 9.3°, 9.7°, 16.8°, 20.6°, and 23.5° in the powder X-ray diffraction spectrum of Compound A.

The powder X-ray diffraction spectrum charts of the above three crystal forms are shown in FIGS. 1 to 3. The powder X-ray diffraction spectra of these crystal forms were measured using RINT-Ultima III (manufactured by Rigaku Corporation) (target: Cu, voltage: 40 kV, current: 40 mA, scan speed: 4°/min).

The active ingredient of the controlled-release preparation of the present invention may be an active form of Compound A, which is the compound of the formula:

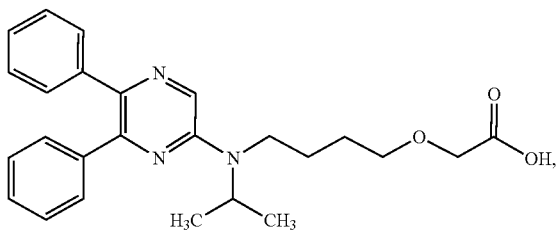 [SMILES: CC(C)N(CCCCOCC(=O)O)c1cnc(-c2ccccc2)c(-c2ccccc2)n1]

hereinafter referred to as "Compound B".

Thus, the controlled-release preparation of the present invention may comprise Compound B, an optical isomer, a pharmaceutically acceptable salt, an amorphous form or a crystal form thereof, or a mixture thereof, as an active ingredient.

The content of Compound A which is the active ingredient of the controlled-release preparation of the present invention is not particularly limited, but is preferably within the range from 0.1 wt % to 3.0 wt %, more preferably within the range from 0.12 wt % to 1.2 wt % with respect to the total weight of the controlled-release preparation.

(B) Water-Soluble Polymer

The "water-soluble polymer" as used herein refers to a polymer which becomes highly viscous when it is dissolved in water. Examples of the water-soluble polymer to be used in the controlled-release preparation of the present invention include polymers whose aqueous solution at a concentration of 10 wt % or less has a viscosity of 1000 mPa·s or more at 25° C. Particularly, the polymer has a viscosity of 1000 mPa·s or more at 25° C., preferably at a concentration of 0.01 to 10 wt %, more preferably at a concentration of 0.1 to 10 wt %, still more preferably at a concentration of 1.0 to 10 wt %.

The water-soluble polymer to be used in the controlled-release preparation of the present invention may be a polymer whose aqueous solution at a concentration of 10 wt % or less has a viscosity in the range of 1000 to 2000 mPa·s at 25° C.

For the water-soluble polymer to be used in the controlled-release preparation of the present invention, if the viscosity of an aqueous solution of the polymer at a concentration of 10 wt % or less exceeds 2000 mPa·s at 25° C., the concentration of the solution can be adjusted to reduce the viscosity to 2000 mPa·s or less.

The viscosity of the aqueous solution of the water-soluble polymer can be measured using a rotary viscometer (Rheometer R/S Plus, manufactured by Brookfield, Inc.) using a sample prepared by dissolving the water-soluble polymer in water and leaving the resulting solution to stand at 25° C. for about 24 hours. The measurement is performed at a measurement temperature of 25° C. and at a rotation speed of 10 rpm, and the viscosity is measured after 300 seconds from the start of the measurement.

Examples of the water-soluble polymer to be used in the controlled-release preparation of the present invention include hypromellose (hereinafter referred to as "HPMC"), hydroxymethyl cellulose, hydroxyethyl cellulose, hydroxypropylcellulose (hereinafter referred to as "HPC"), hydroxyethylmethyl cellulose, carboxymethyl cellulose, carboxymethyl cellulose sodium salt, polyvinyl alcohol (hereinafter referred to as "PVA"), alginic acid, an alkali metal salt of alginic acid, ammonium alginate, carrageenan, xanthan gum, gum Arabic, and polyethylene oxide. Particularly, HPMC, HPC, and PVA are preferred, and HPMC is particularly preferred.

HPMC is a cellulose derivative having a hydroxypropoxyl group and a methoxy group in the molecule. Examples of the HPMC to be used in the controlled-release preparation of the present invention include Metolose® 60SH-4000SR (manufactured by Shin-Etsu Chemical Co., Ltd.), Metolose® 60SH-8000SR (manufactured by Shin-Etsu Chemical Co., Ltd.), Metolose® 65SH-4000SR (manufactured by Shin-Etsu Chemical Co., Ltd.), Metolose® 65SH-15000SR (manufactured by Shin-Etsu Chemical Co., Ltd.), Metolose® 90SH-100SR (manufactured by Shin-Etsu Chemical Co., Ltd.), Metolose® 90SH-4000SR (manufactured by Shin-Etsu Chemical Co., Ltd.), Metolose® 90SH-15000SR (manufactured by Shin-Etsu Chemical Co., Ltd.), and Metolose® 90SH-100000SR (manufactured by Shin-Etsu Chemical Co., Ltd.), and any of these can be obtained as a commercially available product.

HPC is a cellulose derivative having a hydroxypropoxyl group in the molecule. Examples of the HPC to be used in the controlled-release preparation of the present invention include Klucel® HXF (manufactured by Ashland, Inc.), Klucel® MXF (manufactured by Ashland, Inc.), Klucel® GXF (manufactured by Ashland, Inc.), NISSO HPC H (manufactured by Nippon Soda Co., Ltd.), and NISSO HPC VH (manufactured by Nippon Soda Co., Ltd.), and any of these can be obtained as a commercially available product.

PVA is a polymeric compound represented by the following general formula and obtained by saponification of polyvinyl acetate, which is obtained by polymerizing a vinyl acetate monomer.

[Chem. 2]

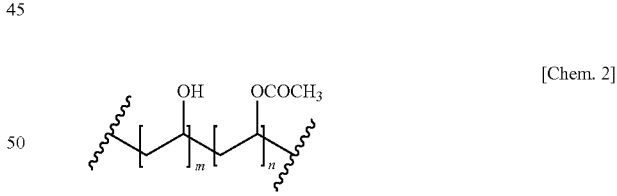

(In the formula, m and n each represent a positive integer.)

Examples of the PVA to be used in the controlled-release preparation of the present invention include Gohsenol® EG-48P (manufactured by Nippon Synthetic Chemical Industry Co., Ltd.) and Parteck® SRP80 (manufactured by Merck, Inc.), and either of these can be obtained as a commercially available product.

Examples of the alkali metal salt of alginic acid include sodium alginate and potassium alginate.

The content of the water-soluble polymer in the controlled-release preparation of the present invention is not particularly limited, an upper limit is, for example, 70 wt %, 40 wt %, 30 wt %, 25 wt %, or 15 wt % with respect to the total weight of the controlled-release preparation, a lower limit is, for example, 5 wt %, 15 wt %, 25 wt %, 30 wt % or 40 wt % with respect to the total weight of the controlled-release preparation, and the upper limit and lower limit can be used in combination. Particularly, for example, it is suitably 5 wt % or more, and is preferably within the range from 5 wt % to 70 wt % with respect to the total weight of the controlled-release preparation.

(C) Functional Starch

In one embodiment of the "functional starch" in this description, a starch whose viscosity increases when it comes into contact with water, such as pregelatinized starch, can be exemplified. Specific examples thereof include starches whose aqueous suspension at 7 wt % has a viscosity at 25° C. within the range from 100 mPa·s to 1500 mPa·s, preferably within the range from 300 mPa·s to 1000 mPa·s. Especially, a pregelatinized starch whose aqueous suspension at 7 wt % has a viscosity at 25° C. within the range from 100 mPa·s to 1500 mPa·s, and more preferably a pregelatinized starch whose aqueous suspension at 7 wt % has a viscosity within the range from 300 mPa·s to 1000 mPa·s is preferred.

The viscosity of the aqueous suspension at 7 wt % can be measured using a rotary viscometer (Rheometer R/S Plus, manufactured by Brookfield, Inc.) using a sample prepared by dispersing the starch in water with sufficient stirring and leaving the resulting dispersion to stand at 25° C. for about hours. The measurement is performed at a measurement temperature of 25° C. and at a rotation speed of 10 rpm, and the viscosity is measured after 300 seconds from the start of the measurement.

As another example of the "functional starch" as used herein, a starch which forms a gel which does not disintegrate in water can be exemplified. Particularly, a starch which does not disintegrate even after 1 hour in a disintegration test using an auxiliary disk according to the Japanese Pharmacopoeia 17th edition when the starch is subjected to compression molding is preferred. More preferred is a starch which does not disintegrate even after 1 hour in a disintegration test using an auxiliary disk according to the Japanese Pharmacopoeia 17th edition when a mixture of the starch and a saccharide at a weight ratio of 1:1 is subjected to compression molding.

Here, the "compression molding" refers, for example, to a process in which 190 mg of a starch or 190 mg of a mixture of a starch and a saccharide is compressed at 1000 kgf into a cylindrical shape with a diameter of 8 mm using AUTOGRAPH AG-50kNXD (manufactured by Shimadzu Corporation).

As the "saccharide", for example, D-mannitol or lactose hydrate can be exemplified.

Further, as another example of the "functional starch" in this description, a starch which is dissolved in water or has a water retention capacity within the range from 700% to 1400% when it comes into contact with water can be exemplified. Particularly, a starch having a water retention capacity within the range from 900% to 1300% is preferred.

The "water retention capacity" can be determined as follows.

The dried powder of starch [$W_0$ (g)] is dispersed in pure water, followed by shaking for 24 hours, and then centrifugation (3000 G, 10 minutes) of the resulting dispersion. Immediately thereafter, the upper layer is discarded and the starch which retained water is remained in the lower layer. The weight of the starch which retains water (the starch and pure water retained by the starch) [$W$ (g)] is measured. The water retention capacity is calculated according to the following equation.

$$\text{Water retention capacity (\%)} = 100 \times [W - W_0]/W_0$$

When the pure water and the powder component are not separated after the centrifugation, the starch is regarded as having been dissolved.

Examples of the "functional starch" to be used in the controlled-release preparation of the present invention include pregelatinized starch (see Japanese Pharmaceutical Excipients 2018), such as SWELSTAR® MX-1 (manufactured by Asahi Kasei Corporation), SWELSTAR® WB-1 (manufactured by Asahi Kasei Corporation), Nisshoku Alstar® E (manufactured by Nihon Shokuhin Kako Co., Ltd.), Tapioca alpha NTP (manufactured by Sanwa Cornstarch Co., Ltd.), Tapioca alpha TP-2 (manufactured by Sanwa Cornstarch Co., Ltd.), Corn alpha Y (manufactured by Sanwa Cornstarch Co., Ltd.), and Amycol® C. (manufactured by Nippon Starch Chemical Co., Ltd.), and any of these can be obtained as a commercially available product.

The content of the functional starch in the controlled-release preparation of the present invention is not particularly limited, but is suitably, for example, 15 wt % or more, and is preferably within the range from 15 wt % to 70 wt %, more preferably within the range from 15 wt % to 60 wt %, further more preferably within the range from 15 wt % to 45 wt %, further particularly within the range from 15 wt % to 25 wt % with respect to the total weight of the controlled-release preparation.

The total amount of the water-soluble polymer and the functional starch contained in the controlled-release preparation of the present invention is not particularly limited, but is suitably 25 wt % or more, and is preferably within the range from 25 wt % to 85 wt % with respect to the total weight of the controlled-release preparation.

(D) Alkaline Substance

Examples of "alkaline substance" to be used in the controlled-release preparation of the present invention include substances whose aqueous solution at 0.1 wt % has a pH of 10 or more. Particularly, a substance whose aqueous solution at 0.1 wt % has a pH within the range from 10 to 13 is preferred, and a substance whose aqueous solution at 0.1 wt % has a pH within the range from 10 to 12.5 is more preferred.

Examples of the "alkaline substance" to be used in the controlled-release preparation of the present invention include dried sodium carbonate, potassium carbonate, calcium hydroxide, magnesium hydroxide, magnesium oxide, and meglumine. Particularly, dried sodium carbonate is preferred.

The "alkaline substance" to be used in the controlled-release preparation of the present invention can increase the pH of the controlled-release preparation of the present invention to 10 or more. Particularly, a substance which increases the pH of the preparation to a value within the range from 10 to 13 is preferred, and a substance which increases the pH of the preparation to a value within the range from 10 to 12 is more preferred.

Here, the "pH of the preparation" refers to a pH value of the supernatant, which is obtained by powdering the controlled-release preparation of the present invention, dispersing the resulting powder in a mixed liquid of 3 mL of methanol and 7 mL of pure water, followed by centrifugation. In the measurement of the pH, for example, a pH meter HM-30R (manufactured by DKK-TOA Corporation) can be used. When the weight of the preparation is 100 mg or less, 100 mg of the powder is weighed and the measurement is performed.

The amount of the alkaline substance in the controlled-release preparation of the present invention is not particularly limited, but is suitably, for example, within the range from 1 wt % to 15 wt %, preferably within the range from 1 wt % to 10 wt %, more preferably within the range from 3 wt % to 10 wt % with respect to the total weight of the controlled-release preparation.

(E) Other Additives

In the controlled-release preparation of the present invention, other than the above-mentioned components, pharmaceutically acceptable additives can be blended as long as the effect of the present invention is not inhibited. For example, an additive such as an excipient, a binder, a disintegrating agent, a fluidizing agent, a lubricant, a plasticizer, a coloring agent, a taste masking agent, or a flavoring agent can be blended therein in an appropriate amount as needed. These additives may be used alone or two or more of these additives may be used in combination.

The amount of the additives in the controlled-release preparation of the present invention is not particularly limited, but is suitably, for example, within the range from 15 wt % to 75 wt % with respect to the total weight of the controlled-release preparation.

Examples of the excipient to be used in the controlled-release preparation of the present invention include lactose hydrate, D-mannitol, cornstarch, crystalline cellulose, sucrose, erythritol, and isomaltose. These excipients may be used alone or two or more of these excipients may be used in combination. Particularly, D-mannitol is preferred.

Examples of the D-mannitol to be used in the controlled-release preparation of the present invention include Mannit C (manufactured by Mitsubishi Shoji Foodtech Co., Ltd.), Mannit P (manufactured by Mitsubishi Shoji Foodtech Co., Ltd.), Mannit S (manufactured by Mitsubishi Shoji Foodtech Co., Ltd.), Pearlitol® 25C (manufactured by Roquette Pharma), Pearlitol® 50C (manufactured by Roquette Pharma), Pearlitol® 160C (manufactured by Roquette Pharma), Nonpareil® 108 (100) (Freund Corporation), and Nonpareil® 108 (200) (manufactured by Freund Corporation), each of which can be obtained as a commercially available product. Particularly, Mannit P, Mannit S, Pearlitol® 50C, and Pearlitol® 160C are preferred.

Examples of the cornstarch to be used as the excipient in the controlled-release preparation of the present invention include Nisshoku Cornstarch W (manufactured by Nihon Shokuhin Kako Co., Ltd.), which can be obtained as a commercially available product.

Examples of the crystalline cellulose to be used as the excipient in the controlled-release preparation of the present invention include Ceolus® PH-101 (manufactured by Asahi Kasei Corporation), Ceolus® UF-711 (manufactured by Asahi Kasei Corporation), and Ceolus® KG-1000 (manufactured by Asahi Kasei Corporation), each of which can be obtained as a commercially available product.

Examples of the binder to be used in the controlled-release preparation of the present invention include gelatin, pullulan, HPC, methyl cellulose, polyvinylpyrrolidone, macrogol, gum Arabic, dextran, PVA, and HPMC.

Examples of the HPC to be used as the binder in the controlled-release preparation of the present invention include NISSO HPC-L (manufactured by Nippon Soda Co., Ltd.), NISSO HPC-SL (manufactured by Nippon Soda Co., Ltd.), and NISSO HPC-SSL (manufactured by Nippon Soda Co., Ltd.), each of which can be obtained as a commercially available product.

Examples of the HPMC to be used as the binder in the controlled-release preparation of the present invention include TC-5R (manufactured by Shin-Etsu Chemical Co., Ltd.), which can be obtained as a commercially available product.

Examples of the PVA to be used as the binder in the controlled-release preparation of the present invention include Gohsenol (registered trademark) EG-05P (manufactured by Nippon Synthetic Chemical Industry Co., Ltd.), which can be obtained as a commercially available product.

Examples of the disintegrating agent to be used in the controlled-release preparation of the present invention include carmellose, carmellose calcium, carmellose sodium, croscarmellose sodium, sodium starch glycolate, crospovidone, a cation exchange resin, partially pregelatinized starch, and low-substituted hydroxypropylcellulose.

Examples of the fluidizing agent to be used in the controlled-release preparation of the present invention include light anhydrous silicic acid, hydrous silicon dioxide, synthetic aluminum silicate, and magnesium aluminometasilicate.

Examples of the lubricant to be used in the controlled-release preparation of the present invention include stearic acid, magnesium stearate, calcium stearate, sodium stearyl fumarate, talc, waxes, DL-leucine, sodium lauryl sulfate, magnesium lauryl sulfate, macrogol, and light anhydrous silicic acid, and particularly, magnesium stearate and sodium stearyl fumarate are preferred.

Examples of the plasticizer to be used in the controlled-release preparation of the present invention include triethyl citrate, propylene glycol, and macrogol.

Examples of the coloring agent to be used in the controlled-release preparation of the present invention include titanium oxide, talc, ferric oxide, yellow ferric oxide, Food Yellow No. 4, and Food Yellow No. 4 Aluminum Lake.

Examples of the taste masking agent to be used in the controlled-release preparation of the present invention include fructose, xylitol, glucose, and DL-malic acid.

Examples of the flavoring agent to be used in the controlled-release preparation of the present invention include 1-menthol and peppermint.

(F) Shape of Controlled-Release Preparation

The shape of the controlled-release preparation of the present invention may be, but not limited to, a circle, an ellipse, a doughnut shape, or the like.

The tablet thickness of the controlled-release preparation of the present invention is not particularly limited, but is suitably, for example, within the range from 1 mm to 10 mm, and is preferably within the range from 2 mm to 9 mm.

The size of the controlled-release preparation of the present invention is not particularly limited, however, for example, the minor axis (in the case of a circular tablet, the diameter) is suitably within the range from 1 mm to 20 mm, and is preferably, for example, within the range from 2 mm to 14 mm.

The weight of the controlled-release preparation of the present invention is not particularly limited, but is suitably within the range from 5 mg to 500 mg, and is preferably within the range from 10 mg to 300 mg.

(G) Release Profile Test

In one embodiment, the controlled-release preparation of the present invention satisfies at least Criteria (x) and (y), preferably all the Criteria (x) to (z) as follows:

Criterion (x): under the conditions of a dissolution test in which 900 mL of a test solution at pH 6.8 is used and a paddle rotation speed is set to 200 rpm, a dissolution rate $(R(x))$ at the time t is within the range of R±15%;

Criterion (y): under the conditions of a dissolution test in which 900 mL of a test solution at pH 5.0 is used and a paddle rotation speed is set to 50 rpm, a dissolution rate (R(y)) at the time t is within the range of R±15%; and Criterion (z): under the conditions of a dissolution test in which 500 mL of a test solution at pH 1.2 is used and a paddle rotation speed is set to 200 rpm, the preparation does not disintegrate at the time t;

wherein t is the time to release about 50% (40 to 60%) of Compound A in the preparation and R is the dissolution rate at the time t, under the conditions of a dissolution test in which 900 mL of a test solution at pH 6.8 is used and the paddle rotation speed is set to 50 rpm.

In the above Criteria (x) to (z), t may be within the range from 2 hours to 24 hours, preferably from 2 hours to 12 hours.

The "dissolution test" as used herein refers to a test according to the dissolution test (Paddle Method) described in the Japanese Pharmacopoeia 17th edition. In the dissolution test, a sinker device is used, and the test is carried out at a liquid temperature of 37° C., unless otherwise specified.

The "test solution at pH 6.8" refers to the "2nd fluid for dissolution test" described in the Japanese Pharmacopoeia 17th edition. The "test solution at pH 5.0" refers to a diluted McIlvaine buffer solution, prepared by adjusting the pH to 5.0 using aqueous 0.05 mol/L disodium hydrogenphosphate and aqueous 0.025 mol/L citric acid (see, "Notification regarding Preliminary Test for Reevaluation concerning Quality of Medical Drugs (Iyakushin No. 549)"). The "test solution at pH 1.2" refers to the "1st fluid for dissolution test" described in the Japanese Pharmacopoeia 17th edition.

In relation to the Criterion (z), the disintegration of preparation is defined as that state in which the preparation does not keep in shape, i.e., the preparation has been dissolved, disappeared, divided or become soft mass having no shape.

(H) Production Method for Controlled-Release Preparation of the Present Invention The controlled-release preparation of the present invention can be produced by a conventional method in the pharmaceutical technical field using the above-mentioned various types of additives.

The controlled-release preparation of the present invention can be produced by, for example, mixing Compound A which is the active ingredient with various types of additives, followed by direct compression molding, or by granulating Compound A which is the active ingredient and various types of additives, followed by compression molding of the resulting granules as such or a mixture of the resulting granules with another additive.

The compression molding method is not particularly limited, and a known device can be appropriately selected, and for example, a method using a device such as a compression testing device, an oil hydraulic press, or a tableting machine, or the like can be exemplified. Examples of the compression testing device include a universal material testing device (AUTOGRAPH, manufactured by Shimadzu Corporation). Examples of the tableting machine include a rotary tableting machine (Clean Press Correct 12, manufactured by Kikusui Seisakusho, Ltd.).

As for the pressure at the time of compression molding, the conditions suitable for a desired device and a desired compression molded material may be appropriately selected.

Further, a capsule formulation can be produced by filling a capsule with the above-mentioned compression-molded material. As the capsule, a known capsule can be used, and for example, a gelatin capsule and an HPMC capsule can be exemplified. The size of the capsule is not particularly limited as long as the size enables the capsule to be filled with the controlled-release preparation of the present invention, however, capsules No. 00 to No. 5 can be obtained as commercially available products.

The controlled-release preparation of the present invention may be coated by a conventional method in the pharmaceutical technical field as needed. Further, a mark or a letter for discriminating the preparation, or further, a division line for dividing the preparation may be provided.

Here, as a coating base, for example, a sugar coating base and a water-soluble film coating base can be exemplified.

As the sugar coating base, sucrose is used, and further, one or more selected from the group consisting of talc, precipitated calcium carbonate, gelatin, gum Arabic, pullulan, and carnauba wax may be used in combination.

Examples of the water-soluble film coating base include (i) cellulose-based polymers such as hydroxypropylcellulose, hydroxypropylmethyl cellulose, hydroxyethyl cellulose, and methylhydroxyethyl cellulose, (ii) synthetic polymers such as polyvinyl alcohol, polyvinylacetal diethylaminoacetate, aminoalkyl methacrylate copolymer E [Eudragit® E], and polyvinylpyrrolidone, and (iii) polysaccharides such as pullulan.

Two or more of the above-mentioned coating bases may be used as a mixture at an appropriate ratio. Further, a coating additive may be used in a coating process.

Examples of the coating additive include (i) light shielding agents and/or coloring agents such as titanium oxide, talc, and ferric oxide, and (ii) plasticizers such as polyethylene glycol, triethyl citrate, castor oil, and polysorbates.

For example, the controlled-release preparation of the present invention produced by the above-mentioned method may have a strength satisfying the above-mentioned Criterion (z).

(I) Medical Application

The Compound A has an excellent PGI2 receptor agonistic effect and shows various medicinal effects such as a platelet aggregation inhibitory effect, a vasodilating effect, a bronchial smooth muscle dilating effect, a lipid deposition inhibitory effect, and a leukocyte activation inhibitory effect (see, for example, PTL 7 to PTL 12).

Therefore, the controlled-release preparation of the present invention is useful as a preventive agent or a therapeutic agent for transient ischemic attack (TIA), diabetic neuropathy (see, for example, NPL 2), diabetic gangrene (see, for example, NPL 2), a peripheral circulatory disturbance [for example, chronic arterial occlusion (see, for example, NPL 3), intermittent claudication (see, for example, NPL 4), peripheral embolism, vibration syndrome, or Raynaud's disease] (see, for example, NPL 5 and NPL 6), a connective tissue disease [for example, systemic lupus erythematosus, scleroderma (see, for example, PTL 13 and NPL 7), a mixed connective tissue disease, or a vasculitic syndrome], reocclusion/restenosis after percutaneous transluminal coronary angioplasty (PTCA), arteriosclerosis, thrombosis (for example, acute-phase cerebral thrombosis or pulmonary embolism) (see, for example, NPL 6 and NPL 8), hypertension, pulmonary hypertension, an ischemic disease [for example, cerebral infarction or myocardial infarction (see, for example, NPL 9)], angina pectoris (for example, stable angina pectoris or unstable angina pectoris) (see, for example, NPL 10), glomerulonephritis (see, for example, NPL 11), diabetic nephropathy (see, for example, NPL 2), chronic renal failure (see, for example, PTL 14), allergy, bronchial asthma (see, for example, NPL 12), ulcer, pressure ulcer (bedsore), restenosis after coronary intervention such as atherectomy or stent implantation, thrombocytopenia by dialysis, a disease in which fibrogenesis in an organ or a tissue is involved [for example, a renal disease {for example, tubulointerstitial nephritis (see, for example, PTL 15)}, a respiratory disease {for example, interstitial pneumonia (pulmonary fibrosis) (see, for example, PTL 15), a chronic obstructive pulmonary disease (see, for example, NPL 13)}, a digestive disease (for example, hepatocirrhosis, viral hepatitis, chronic pancreatitis, or scirrhous gastric cancer), a cardiovascular disease (for example, myocardial fibrosis), a bone or articular disease (for example, bone marrow fibrosis or rheumatoid arthritis), a skin disease (for example, postoperative cicatrix, burn cicatrix, keloid, or hypertrophic cicatrix), an obstetric disease (for example, uterine fibroid), a urinary disease (for example, prostatic hypertrophy), other diseases (for example, Alzheimer's disease, sclerosing peritonitis, type I diabetes, and postoperative organ adhesion)], erectile dysfunction (for example, diabetic erectile dysfunction, psychogenic erectile dysfunction, psychotic erectile dysfunction, erectile dysfunction due to chronic renal failure, erectile dysfunction after pelvic operation for resection of the prostate, or vascular erectile dysfunction associated with aging or arteriosclerosis), an inflammatory bowel disease (for example, ulcerative colitis, Crohn's disease, intestinal tuberculosis, ischemic colitis, or intestinal ulcer associated with Behcet disease) (see, for example, PTL 16), gastritis, gastric ulcer, an ischemic eye disease (for example, retinal artery occlusion, retinal vein occlusion, or ischemic optic neuropathy), sudden hearing loss, avascular necrosis of bone, an intestinal damage caused by administration of a non-steroidal anti-inflammatory agent (NSAID) (for example, diclofenac, meloxicam, oxaprozin, nabumetone, indomethacin, ibuprofen, ketoprofen, naproxen, or celecoxib) (there is no particular limitation as long as it is a damage occurring in, for example, the duodenum, small intestine, or large intestine, however, for example, a mucosal damage such as erosion or ulcer occurring in the duodenum, small intestine, or large intestine), or symptoms (for example, paralysis, dullness in sensory perception, pain, numbness, or a decrease in walking ability) associated with spinal canal stenosis (for example, cervical spinal canal stenosis, thoracic spinal canal stenosis, lumbar spinal canal stenosis, coexisting cervical and lumbar spinal canal stenosis, or sacral spinal canal stenosis) (see PTL 17).

In addition, the controlled-release preparation of the present invention is also useful as an accelerating agent for gene therapy or angiogenic therapy such as autologous bone marrow transplantation, or an accelerating agent for angiogenesis in restoration of peripheral artery or angiogenic therapy.

Particularly, the controlled-release preparation of the present invention is useful as an agent for the treatment or prevention of diabetic neuropathy, diabetic gangrene, peripheral circulatory disturbance, chronic arterial occlusion, intermittent claudication, scleroderma, thrombosis, pulmonary hypertension, myocardial infarction, angina, glomerulonephritis, diabetic nephropathy, chronic renal failure, bronchial asthma, interstitial pneumonia (pulmonary fibrosis), chronic obstructive pulmonary disease, tubulointerstitial nephritis, inflammatory bowel disease, or symptoms associated with spinal canal stenosis.

(J) Other Active Ingredients

So long as it does not inhibit the effect of the invention, the controlled-release preparation of the present invention may comprise, in addition to the components as described above, a pharmaceutically active ingredient such as an agent for the treatment or prevention of the diseases as described above, an investigational new drug for the diseases as described above, and the like.

(K) Dosage Regimen

So long as it does not inhibit the effect of the invention, the dose of the controlled-release preparation of the present invention may be decided taking into consideration symptoms, age, sex and the like of the subject to be administered, but is usually approximately from 0.05 mg to 5.0 mg of Compound A per adult per day in the case of oral administration, and the dose may be administered once or be divided into 2 to 4 times, preferably once in a day.

So long as it does not inhibit the effect of the invention, the controlled-release preparation of the present invention can be used in combination with another drug for the treatment or prevention or an investigational new drug described above.

(L) Use of Controlled-Release Preparation

In one aspect of the invention, there is provided a use of the controlled-release preparation in the treatment or prevention of the disease described above, a use of the controlled-release preparation in the manufacture of a medicament for the treatment or prevention of the disease described above, a method for the treatment or prevention of the disease described above comprising administering a therapeutically effective amount of the controlled-release preparation to a patient in need thereof. The descriptions provided above with respect to the controlled-release preparation are applied to such use of the controlled-release preparation.

(M) Controlled-Release Composition/Controlled-Release Formulation

The term "controlled-release preparation" can be used interchangeably with the term "controlled-release composition" or "controlled-release formulation". The descriptions provided above with respect to the controlled-release preparation are applied to such controlled-release composition and controlled-release formulation.

EXAMPLES

Hereinafter, the present invention will be described in more detail with reference to Examples and Comparative Examples, however, the scope of the present invention is not limited to the range of these Examples.

(1) Compound A

Compound A used in Examples and Comparative Examples was the Form-I crystal of Compound A described above.

(2) Water-Soluble Polymer

The concentration and the viscosity (mPa·s) of the water-soluble polymer are shown in the following Table 1.

The viscosity (mPa·s) of the water-soluble polymer was measured according to the following method.

<Measurement Method>

The water-soluble polymer was dissolved in water, and the resulting solution was left to stand at 25° C. for about 24 hours to prepare a sample. The viscosity was measured using a rotary viscometer (Rheometer R/S Plus, manufactured by Brookfield, Inc.). The measurement was performed at a measurement temperature of 25° C. and at a rotation speed of 10 rpm, and the viscosity was measured after 300 seconds from the start of the measurement.

The viscosity of the aqueous solution of the water-soluble polymer greatly varies depending on the water-soluble polymer to be used. When the aqueous solution contains the water-soluble polymer at a concentration of 10 wt % or less with respect to the total weight of the solution and the viscosity of the solution was 1000 mPa·s or more, the concentration was adjusted so that the viscosity was from 1000 to 2000 mPa·s, in view of the operability during preparation of a solution.

TABLE 1

| Generic name | Trade Name | Aqueous solution of Water-soluble polymer | |
|---|---|---|---|
| | | Concentration (wt %) | Viscosity (mPa · s) |
| HPMC | Metolose ® 90SH100SR | 5 | 1758 |
| HPMC | Metolose ® 90SH4000SR | 2 | 1536 |
| HPMC | Metolose ® 90SH100000SR | 1.1 | 1243 |
| HPMC | TC-5R ® | 10 | 253 |
| HPC | Klucel ® HXF | 1.5 | 1225 |
| HPC | Klucel ® MXF | 2 | 1381 |
| HPC | NISSO HPC-H | 2 | 1044 |
| HPC | Klucel ® EF | 10 | 449 |
| HPC | NISSO HPC-L | 10 | 390 |
| PVA | Gohsenol ® EG-48P* | 10 | 1568 |
| PVA | Parteck SRP80 | 10 | 1642 |

TABLE 1-continued

| Generic name | Trade Name | Aqueous solution of Water-soluble polymer | |
|---|---|---|---|
| | | Concentration (wt %) | Viscosity (mPa · s) |
| PVA | Gohsenol ® EG-05P | 10 | 32 |
| Povidone | Kollidon ® 30 | 10 | 0 |

*The finely pulverized material was used.
[Median size: 38 μm, Laser diffraction/Scattering particle size distribution measuring device LA-950 (Dry): HORIBA, Ltd.]

(3) Functional Starch

The viscosity (mPa·s) of 7 wt % suspension and the water retention capacity (%) of the starch are shown in the following Table 2.

The viscosity (mPa·s) of 7 wt % suspension and the water retention capacity (%) were measured according to the following method.

<Measurement Method for Viscosity (mPa·s) of 7 wt % Suspension of Starch>

The starch was dispersed in water to obtain an aqueous suspension at 7 wt %, and the resulting suspension was well stirred, and then left to stand at 25° C. for about 24 hours to prepare a sample. The sample was gently stirred before measurement, and the viscosity was measured using a rotary viscometer (Rheometer R/S Plus, manufactured by Brookfield, Inc.).

The measurement was performed at a measurement temperature of 25° C. and at a rotation speed of 10 rpm, and a value obtained after 300 seconds from the start of the measurement was determined as the viscosity.

<Measurement Method for Water Retention Capacity (%) of Starch>

The powdered starch [$W_0$ (g)] (about 1 g) which had been dried at about 80° C. for 5 hours was dispersed in pure water, followed by shaking for 24 hours and centrifugation (3000 G, minutes). Immediately thereafter, the upper layer was discarded and the starch which retained water was remained in the lower layer. The weight of the starch which retained water (the starch and pure water retained by the starch) [W (g)] was measured. The water retention capacity was calculated according to the following equation.

Water retention capacity (%)=100×[$W-W_0$]/$W_0$

The value of the water retention capacity was rounded down by discarding the tens place and expressed in hundreds. When the pure water and the powder component were not separated after the centrifugation, the starch was regarded as having been dissolved.

TABLE 2

| Generic name | Trade Name | Viscosity of 7 wt % Suspension (mPa · s) | Water Retention Capacity (%) |
|---|---|---|---|
| Cornstarch | Nisshoku Cornstarch W | 0 | 0 |
| Pregelatinized starch | SWELSTAR ® PD-1 | 13 | 600 |
| Pregelatinized starch | SWELSTAR ® WB-1 | 468 | 1200 |
| Pregelatinized starch | SWELSTAR ® MX-1 | 636 | 1200 |
| Pregelatinized starch | Nisshoku Alstar ® E | 454 | 900 |
| Pregelatinized starch | Amycol ® C | 1421 | 1100 |
| Pregelatinized starch | Tapioca alpha NTP | 664 | 1400 |
| Pregelatinized starch | Tapioca alpha TP2 | 199 | Dissolved |
| Pregelatinized starch | Corn alpha Y | 306 | 1200 |
| Partly pregelatinized starch | PCS ® PC-10 | 0 | 600 |
| Oxidized starch | Lustergen ® FO | 0 | — |
| Dextrin | Pinedex ® #1 | 0 | — |

—: Unmeasured

The results of examination of the disintegration property after 1 hour of the compression molded starch and the compression molded mixture of the starch and the saccharide are shown in the following Table 3.

The disintegration property after 1 hour of the compression molded starch and the compression molded mixture of the starch and the saccharide were measured according to the following method.

<Measurement Method>

190 mg of the starch and 190 mg of the mixture of the starch and the saccharide at a weight ratio of 1:1 were compressed, respectively, at 1000 kgf to obtain compression molded materials in a cylindrical shape with a diameter of 8 mm (lens surface, 12R). These compression molded materials were subjected to a disintegration test using an auxiliary disk according to the disintegration test method (test liquid: water) of the Japanese Pharmacopoeia 17th edition and it was determined whether disintegration occurred after 1 hour from the start of the test.

The saccharide used was D-mannitol (Mannit P (manufactured by Mitsubishi Shoji Foodtech Co., Ltd.)) or lactose hydrate (Pharmatose® 200M (DFE Pharma)).

TABLE 3

| Generic name | Trade Name | Disintegration after 1 hour Starch only | Starch and Saccharide (1:1 wt mixture) |
|---|---|---|---|
| Cornstarch | Nisshoku Cornstarch W | x | x |
| Pregelatinized starch | SWELSTAR ® PD-1 | x | x |
| Pregelatinized starch | SWELSTAR ® WB-1 | o | o |
| Pregelatinized starch | SWELSTAR ® MX-1 | o | o |
| Pregelatinized starch | Nisshoku Alstar ® E | o | o |
| Pregelatinized starch | Amycol ® C | o | o |
| Pregelatinized starch | Tapioca alpha NTP | o | o |
| Pregelatinized starch | Tapioca alpha TP2 | o | o |
| Pregelatinized starch | Corn alpha Y | o | o |
| Partly pregelatinized starch | PCS ® PC-10 | x | x |
| Oxidized starch | Lustergen ® FO | x | x |
| Dextrin | Pinedex ® #1 | x | x | o: Not disintegrated
x: Disintegrated (4) Alkaline Substance

The pH of the alkaline substance is shown in the following Table 4.

The pH of the alkaline substance was measured according to the following method.

<Measurement Method>

The alkaline substance was dissolved (or dispersed) in water at 0.1 wt %, and the pH of the solution (or the dispersion) was determined using a pH METER HM-30R (manufactured by DKK-TOA Corporation).

TABLE 4

| Generic name | Manufacturer | pH |
|---|---|---|
| Dried sodium carbonate | Nacalai Tesque, Inc | 11.0 |
| Potassium carbonate | Nacalai Tesque, Inc | 10.9 |
| Calcium carbonate | Nacalai Tesque, Inc | 9.8 |
| Sodium bicarbonate | Asahi glass Co., Ltd. | 8.5 |
| Calcium hydroxide | Nacalai Tesque, Inc | 12.2 |
| Magnesium hydroxide | Tomita Pharmaceutical Co., Ltd. | 10.3 |
| Magnesium oxide | Tomita Pharmaceutical Co., Ltd. | 10.7 |
| Trisodium citrate | Wako Pure Chemical Industries, Ltd. | 8.3 |
| Sodium acetate | Nacalai Tesque, Inc | 7.6 |
| Sodium hydrogen phosphate | Nacalai Tesque, Inc | 9.2 |
| Meglumine | Merck Ltd. | 10.6 |

Test Example 1

Tablets shown in Table 5 were produced, and these tablets were evaluated.

<Preparation of Tablet>

The compositions of the tablet are shown in the following Table 5. The components were weighed and mixed in a mortar, and the resulting mixed powder was compressed at 1000 kgf using AUTOGRAPH AG-50kNXD (manufactured by Shimadzu Corporation) to obtain a tablet with diameter of 8 mm.

TABLE 5

| Component | Comparative Example 1-1 | Comparative Example 1-2 | Comparative Example 1-3 | Comparative Example 1-4 |
|---|---|---|---|---|
| Compound A | 0.4 mg | 0.4 mg | 0.4 mg | 0.4 mg |
| D-Mannitol Mannit P (Mitsubishi Shoji Foodtech Co., Ltd.) | 131.65 mg | 131.65 mg | 131.65 mg | 131.65 mg |
| Water-Soluble Polymer: HPMC METOLOSE ® 90SH-4000SR | 57 mg | — | — | — |
| Water-Soluble Polymer: HPC Klucel ® HXF | — | 57 mg | — | — |
| Functional Starch: pregelatinized starch SWELSTAR ® MX-1 | — | — | 57 mg | — |
| Polyvinyl acetate/Polyvinylpyrrolidone Kollidon ® SR | — | — | — | 57 mg |
| Magnesium stearate Magnesium stearate (Special grade) (Taihei Chemical Industrial Co., Ltd.) | 0.95 mg | 0.95 mg | 0.95 mg | 0.95 mg |
| Total | 190 mg | 190 mg | 190 mg | 190 mg |

<Evaluation Method>

The tablets shown in Table 5 were evaluated according to the paddle method of the dissolution test of the Japanese Pharmacopoeia 17th edition. In the test, a sinker device was used.

The time to release about 50% (40 to 60%) of Compound A in the tablet was defined as the test time t under the conditions of the dissolution test in which 900 mL of the test solution at pH 6.8 was used and the paddle rotation speed was set to 50 rpm, and the dissolution rate at the test time t was defined as R, and the tablets were evaluated with respect to the Criteria (x) to (z) as follows.

Criterion (x):

Under the conditions of the dissolution test in which 900 mL of the test solution at pH 6.8 was used and the paddle rotation speed was set to 200 rpm, a case where the dissolution rate $R_{(x)}$ at the test time t was within the range of R±15% was determined to be "suitable", and a case where it was outside the range of R±15% was determined to be "unsuitable".

Criterion (y):

Under the conditions of the dissolution test in which 900 mL of the test solution at pH 5.0 was used and the paddle rotation speed was set to 50 rpm, a case where the dissolution rate $R_{(y)}$ at the test time t was within the range of R±15% was determined to be "suitable", and a case where it was outside the range of R±15% was determined to be "unsuitable".

Criterion (z):

Under the conditions of the dissolution test in which 500 mL of the test solution at pH 1.2 was used and the paddle rotation speed was set to 200 rpm, a case where the disintegration of the tablet does not occur at the test time t was determined to be "suitable", and a case where the disintegration of the tablet occurs at the time t was determined to be "unsuitable".

As for overall evaluation, a case which was determined to be "suitable" for all the Criteria (x) to (z) was determined to be "suitable", and the other cases were determined to be "unsuitable".

<Results>

The evaluation results of Comparative Example 1-1, Comparative Example 1-2, Comparative Example 1-3, and Comparative Example 1-4 are shown in Table 6.

As shown in Table 6, the tablets in which HPMC, HPC, pregelatinized starch, or Polyvinyl acetate/Polyvinylpyrrolidone, each of which is generally used as a sustained-release base, was contained alone satisfied not all of the Criteria (x) to (z).

TABLE 6

| | Evaluation for Criteria | | | |
|---|---|---|---|---|
| Evaluation item | Comparative Example 1-1 | Comparative Example 1-2 | Comparative Example 1-3 | Comparative Example 1-4 |
| Test time: t (hours) | 8 | 12 | 6 | 2 |
| Dissolution rate: R (%) | 55 | 49 | 51 | 50 |
| Evaluation for Criteria (x) | unsuitable | unsuitable | suitable | unsuitable |
| Dissolution rate: $R_{(x)}$ (%) | 87 | 99 | 55 | 80 |
| Evaluation for Criteria (y) | unsuitable | unsuitable | unsuitable | unsuitable |
| Dissolution rate: $R_{(y)}$ (%) | 30 | 18 | 2 | 13 |
| Evaluation for Criteria (z) | suitable | — | unsuitable | — |
| Disintegration | Not Occurred | — | Occurred | — |
| Overall evaluation | unsuitable | unsuitable | unsuitable | unsuitable |

—: Unmeasured

Test Example 2

Tablets shown in Table 7 were produced, and these tablets were evaluated.

<Preparation of Tablet>

The compositions of the tablets are shown in Table 7. Tablets having a tablet diameter of 8 mm were obtained according to the method as described in Test Example 1.

TABLE 7

| | Composition | | | |
|---|---|---|---|---|
| Component | Comparative Example 2-1 | Comparative Example 2-2 | Example 2-1 | Example 2-2 |
| Compound A | 0.4 mg | 0.4 mg | 0.4 mg | 0.4 mg |
| D-Mannitol Mannit P (Mitsubishi Shoji Foodtech Co., Ltd.) | 93.65 mg | 93.65 mg | 84.15 mg | 84.15 mg |
| Water-Soluble Polymer: HPMC Metolose ® 90SH-4000SR | 57 mg | — | 57 mg | — |
| Water-Soluble Polymer: PVA Gohsenol ® EG-48P* | — | 57 mg | — | 57 mg |
| Functional Starch: Pregelatinized starch SWELSTAR ® MX-1 | 38 mg | 38 mg | 38 mg | 38 mg |

TABLE 7-continued

| Component | Composition | | | |
|---|---|---|---|---|
| | Comparative Example 2-1 | Comparative Example 2-2 | Example 2-1 | Example 2-2 |
| Alkaline Substance: Dried sodium carbonate Dried sodium carbonate (Powdered) (Takasugi Pharmaceutical Co., Ltd.) | — | — | 9.5 mg | 9.5 mg |
| Magnesium stearate Magnesium stearate (Special grade) (Taihei Chemical Industrial Co., Ltd.) | 0.95 mg | 0.95 mg | 0.95 mg | 0.95 mg |
| Total | 190 mg | 190 mg | 190 mg | 190 mg |

*The finely pulverized material was used.
[Median size: 38 μm, Laser diffraction/Scattering particle size distribution measuring device LA-950 (Dry): HORIBA, Ltd.]

<Evaluation Method>
The tablets shown in Table 7 were evaluated in the same manner as in Test Example 1, and also the pH of these preparations was measured according to the following method.

<Measurement Method for pH of Preparation>
One preparation was powdered, and the resulting powder was dispersed in a mixed liquid of 3 mL of methanol and 7 mL of pure water, followed by centrifugation, and the pH of the supernatant was measured using a pH meter HM-30R (manufactured by DKK-TOA Corporation).

<Results>
The evaluation results of Comparative Example 2-1, Comparative Example 2-2, Example 2-1, and Example 2-2 are shown in Table 8. Further, the dissolution profile of Comparative Example 2-1 is shown in FIG. 4, the dissolution profile of Comparative Example 2-2 is shown in FIG. 5, the dissolution profile of Example 2-1 is shown in FIG. 6, and the dissolution profile of Example 2-2 is shown in FIG. 7.

As shown in Table 8, the tablets which contained the water-soluble polymer (HPMC or PVA) and the functional starch, but did not contain the alkaline substance satisfied not all of the Criteria (x) to (z).

On the other hand, the tablets which contained the water-soluble polymer (HPMC or PVA), the functional starch and the alkaline substance satisfied all the Criteria (x) to (z).

TABLE 8

| Evaluation item | Evaluation for Criteria | | | |
|---|---|---|---|---|
| | Comparative Example 2-1 | Comparative Example 2-2 | Example 2-1 | Example 2-2 |
| Test time: t (hours) | 12 | 8 | 8 | 6 |
| Dissolution rate: R (%) | 52 | 52 | 54 | 50 |
| Evaluation for Criteria (x) | unsuitable | unsuitable | suitable | suitable |
| Dissolution rate: $R_{(x)}$ (%) | 73 | 93 | 61 | 59 |
| Evaluation for Criteria (y) | unsuitable | unsuitable | suitable | suitable |
| Dissolution rate: $R_{(y)}$ (%) | 14 | 12 | 49 | 44 |
| Evaluation for Criteria (z) | suitable | unsuitable | suitable | suitable |
| Disintegration | Not Occurred | Occurred | Not Occurred | Not Occurred |

TABLE 8-continued

| Evaluation item | Evaluation for Criteria | | | |
|---|---|---|---|---|
| | Comparative Example 2-1 | Comparative Example 2-2 | Example 2-1 | Example 2-2 |
| Overall evaluation | unsuitable | unsuitable | suitable | suitable |
| pH of Preparation | 7.4 | 7.3 | 11.4 | 10.7 |

Test Example 3

Tablets shown in Table 9 were produced, and these tablets were evaluated.

<Preparation of Tablet>
The compositions of the tablets are shown in Table 9. Tablets having a tablet diameter of 8 mm were obtained according to the method as described in Test Example 1.

TABLE 9

| Component | Composition | |
|---|---|---|
| | Comparative Example 3-1 | Example 3-1 |
| Compound A | 0.4 mg | 0.4 mg |
| D-Mannitol Mannit P (Mitsubishi Shoji Foodtech Co., Ltd.) | 112.65 mg | 93.65 mg |
| Water-Soluble Polymer: HPMC Metolose ® 90SH-4000SR | 57 mg | 57 mg |
| Functional Starch: Pregelatinized Starch SWELSTAR ® MX-1 | 9.5 mg | 28.5 mg |
| Alkaline Substance: Dried sodium carbonate Dried sodium carbonate (Powdered) (Takasugi Pharmaceutical Co., Ltd.) | 9.5 mg | 9.5 mg |
| Magnesium stearate Magnesium stearate (Special grade) (Taihei Chemical Industrial Co., Ltd.) | 0.95 mg | 0.95 mg |
| Total | 190 mg | 190 mg |

<Evaluation Method>

The tablets shown in Table 9 were evaluated in the same manner as in Test Example 2.

<Results>

The evaluation results of Comparative Example 3-1 and Example 3-1 are shown in Table 10.

As shown in Table 10, among the tablets containing the water-soluble polymer, the functional starch and the alkaline substance, Comparative Example 3-1 containing 5 wt % of the functional starch satisfied not all of the Criteria (x) to (z), while Example 3-1 containing 15 wt % of the functional starch satisfied all the Criteria (x) to (z).

TABLE 10

| | Evaluation for Criteria | |
|---|---|---|
| Evaluation item | Comparative Example 3-1 | Example 3-1 |
| Test time: t (hours) | 6 | 6 |
| Dissolution rate: R (%) | 56 | 47 |
| Evaluation for Criteria (x) | unsuitable | suitable |
| Dissolution rate: $R_{(x)}$ (%) | 80 | 58 |
| Evaluation for Criteria (y) | suitable | suitable |
| Dissolution rate: $R_{(y)}$ (%) | 56 | 42 |
| Evaluation for Criteria (z) | suitable | suitable |
| Disintegration | Not Occurred | Not Occurred |
| Overall evaluation | unsuitable | suitable |
| pH of Preparation | 11.3 | 11.3 |

Test Example 4

Tablets shown in Table 11 were produced, and these tablets were evaluated.

<Preparation of Tablet>

The compositions of the tablets are shown in Table 11. Tablets having a tablet diameter of 8 mm were obtained according to the method as described in Test Example 1.

TABLE 11

| | Composition | | | |
|---|---|---|---|---|
| Component | Comparative Example 4-1 | Comparative Example 4-2 | Comparative Example 4-3 | Comparative Example 4-4 |
| Compound A | 0.4 mg | 0.4 mg | 0.4 mg | 0.4 mg |
| D-Mannitol Mannit P (Mitsubishi Shoji Foodtech Co., Ltd.) | 84.15 mg | 84.15 mg | 84.15 mg | 84.15 mg |
| Water-Soluble Polymer: HPMC Metolose ® 90SH-4000SR | — | — | 57 mg | 57 mg |
| Water-Soluble Polymer: PVA Gohsenol ® EG-48P* | — | 57 mg | — | — |
| Polyvinyl acetate/Polyvinylpyrrolidone Kollidon ® SR | 57 mg | — | — | — |
| Functional Starch: Pregelatinized starch SWELSTAR ® MX-1 | 38 mg | — | — | — |
| Hardened Oil Lubriwax ® 101 | — | 38 mg | — | — |
| Crystalline cellulose Ceolus ® PH101 | — | — | 38 mg | — |
| Ethyl cellulose Ethocel ® STD 7P | — | — | — | 38 mg |
| Alkaline Substance: Dried sodium carbonate Dried sodium carbonate (Powdered) (Takasugi Pharmaceutical Co., Ltd.) | 9.5 mg | 9.5 mg | 9.5 mg | 9.5 mg |
| Magnesium stearate Magnesium stearate (Special grade) (Taihei Chemical Industrial Co., Ltd.) | 0.95 mg | 0.95 mg | 0.95 mg | 0.95 mg |
| Total | 190 mg | 190 mg | 190 mg | 190 mg |

*The finely pulverized material was used.
[Median size: 38 μm, Laser diffraction/Scattering particle size distribution measuring device LA-950 (Dry): HORIBA, Ltd.]

<Evaluation Method>

The tablets shown in Table 11 were evaluated in the same manner as in Test Example 1.

<Results>

The evaluation results of Comparative Example 4-1, Comparative Example 4-2, Comparative Example 4-3, and Comparative Example 4-4 are shown in Table 12.

As shown in Table 12, Comparative Example 4-1 which contained the functional starch and the alkaline substance, but did not contain the water-soluble polymer, and Comparative Example 4-2, Comparative Example 4-3 and Comparative Example 4-4, each of which contained the water-soluble polymer and the alkaline substance, but did not contain the functional starch, satisfied not all of the Criteria (x) to (z).

TABLE 12

| | Evaluation for Criteria | | | |
|---|---|---|---|---|
| Evaluation item | Comparative Example 4-1 | Comparative Example 4-2 | Comparative Example 4-3 | Comparative Example 4-4 |
| Test time: t (hours) | 2 | 2 | 6 | 8 |
| Dissolution rate: R (%) | 42 | 41 | 56 | 51 |
| Evaluation for Criteria (x) | unsuitable | unsuitable | unsuitable | unsuitable |
| Dissolution rate: $R_{(x)}$ (%) | 83 | 92 | 74 | 73 |
| Evaluation for Criteria (y) | unsuitable | suitable | suitable | unsuitable |
| Dissolution rate: $R_{(y)}$ (%) | 18 | 38 | 49 | 30 |
| Evaluation for Criteria (z) | — | — | — | — |
| Disintegration | — | — | — | — |
| Overall evaluation | unsuitable | unsuitable | unsuitable | unsuitable |

—: Unmeasured

Test Example 5

Tablets shown in Table 13 were produced, and these tablets were evaluated.

<Preparation of Tablet>

The compositions of the tablets are shown in Table 13. Tablets having a tablet diameter of 8 mm were obtained according to the method as described in Test Example 1.

TABLE 13

| | Composition | | |
|---|---|---|---|
| Component | Comparative Example 5-1 | Comparative Example 5-2 | Example 5-1 |
| Compound A | 0.4 mg | 0.4 mg | 0.4 mg |
| D-Mannitol Mannit P (Mitsubishi Shoji Foodtech Co., Ltd.) | 46.15 mg | 65.15 mg | 46.15 mg |
| Water-Soluble Polymer: HPMC Metolose ® 90SH-4000SR | 19 mg | — | 19 mg |
| Functional Starch: Pregelatinized starch Amycol ® C | — | 114 mg | 114 mg |
| Pregelatinized starch SWELSTAR ® PD-1 | 114 mg | — | — |
| Alkaline Substance: Dried sodium carbonate Dried sodium carbonate (Powdered) (Takasugi Pharmaceutical Co., Ltd.) | 9.5 mg | 9.5 mg | 9.5 mg |
| Magnesium stearate Magnesium stearate (Special grade) (Taihei Chemical Industrial Co., Ltd.) | 0.95 mg | 0.95 mg | 0.95 mg |
| Total | 190 mg | 190 mg | 190 mg |

<Evaluation Method>

The tablets shown in Table 13 were evaluated in the same manner as in Test Example 2.

<Results>

The evaluation results of Comparative Example 5-1, Comparative Example 5-2, and Example 5-1 are shown in Table 14.

As shown in Table 14, Comparative Example 5-1 which contained the water-soluble polymer, pregelatinized starch which does not correspond to the functional starch, and the alkaline substance showed a dissolution rate of 70% or more after 2 hours, and thus, did not show a sustained-release property.

Further, Comparative Example 5-2 which contained the functional starch and the alkaline substance, but did not contain the water-soluble polymer did not satisfy all the Criteria (x) to (z), while Example 5-1 which further contained the water-soluble polymer satisfied all the Criteria (x) to (z).

TABLE 14

| | Evaluation for Criteria | | |
|---|---|---|---|
| Evaluation item | Comparative Example 5-1 | Comparative Example 5-2 | Example 5-1 |
| Test time: t (hours) | 2 | 4 | 8 |
| Dissolution rate: R (%) | 70 or more | 59 | 47 |

TABLE 14-continued

| | Evaluation for Criteria | | |
|---|---|---|---|
| Evaluation item | Comparative Example 5-1 | Comparative Example 5-2 | Example 5-1 |
| Evaluation for Criteria (x) | — | unsuitable | suitable |
| Dissolution rate: $R_{(x)}$ (%) | — | 76 | 58 |
| Evaluation for Criteria (y) | — | unsuitable | suitable |
| Dissolution rate: $R_{(y)}$ (%) | — | 42 | 42 |
| Evaluation for Criteria (z) | — | unsuitable | suitable |
| Disintegration | — | Occurred | Not Occurred |
| Overall evaluation | unsuitable | unsuitable | suitable |
| pH of Preparation | 11.3 | 11.4 | 11.3 |

—: Unmeasured

Test Example 6

Tablets shown in Table 15 were produced, and these tablets were evaluated.

<Preparation of Tablet>

The compositions of the tablets are shown in Table 15. Tablets having a tablet diameter of 8 mm were obtained according to the method as described in Test Example 1.

TABLE 15

| | Composition | | | |
|---|---|---|---|---|
| Component | Comparative Example 6-1 | Comparative Example 6-2 | Example 6-1 | Example 6-2 |
| Compound A | 0.4 mg | 0.4 mg | 0.4 mg | 0.4 mg |
| D-Mannitol Mannit P (Mitsubishi Shoji Foodtech Co., Ltd.) | 93.65 mg | 84.15 mg | 84.15 mg | 84.15 mg |
| Water-Soluble Polymer: HPMC metolose ® 90SH-4000SR | 19 mg | 19 mg | 19 mg | 19 mg |
| Functional Starch: Pregelatinized starch Tapioca alpha TP2 | 76 mg | — | 76 mg | — |
| Polyvinyl acetate/Polyvinylpyrrolidone Kollidon ® SR | — | 76 mg | — | — |
| Functional Starch: Pregelatinized starch Nisshoku Alster ® E | — | — | — | 76 mg |
| Alkaline Substance: Dried sodium carbonate Dried sodium carbonate (Powdered) (Takasugi Pharmaceutical Co., Ltd.) | — | 9.5 mg | 9.5 mg | 9.5 mg |
| Magnesium stearate Magnesium stearate (Special grade) (Taihei Chemical Industrial Co., Ltd.) | 0.95 mg | 0.95 mg | 0.95 mg | 0.95 mg |
| Total | 190 mg | 190 mg | 190 mg | 190 mg |

<Evaluation Method>

The tablets shown in Table 15 were evaluated in the same manner as in Test Example 2.

<Results>

The evaluation results of Comparative Example 6-1, Comparative Example 6-2, Example 6-1, and Example 6-2, are shown in Table 16.

As shown in Table 16, Comparative Example 6-1 which contained the water-soluble polymer and the functional starch, but did not contain the alkaline substance satisfied not all of the Criteria (x) to (z), while Example 6-1 which further contained the alkaline substance satisfied all the Criteria (x) to (z).

Further, Comparative Example 6-2 which contained the water-soluble polymer, a sustained-release base (Polyvinyl acetate/Polyvinylpyrrolidone) other than the functional starch, and the alkaline substance satisfied not all of the Criteria (x) to (z), while Example 6-2 which contained the water-soluble polymer, the functional starch and the alkaline substance satisfied all the Criteria (x) to (z).

TABLE 16

| | Evaluation for Criteria | | | |
|---|---|---|---|---|
| Evaluation item | Comparative Example 6-1 | Comparative Example 6-2 | Example 6-1 | Example 6-2 |
| Test time: t (hours) | 12 | 4 | 6 | 6 |
| Dissolution rate: R (%) | 50 | 45 | 49 | 55 |
| Evaluation for Criteria (x) | unsuitable | unsuitable | suitable | suitable |
| Dissolution rate: $R_{(x)}$ (%) | 95 | 89 | 52 | 61 |
| Evaluation for Criteria (y) | unsuitable | unsuitable | suitable | suitable |
| Dissolution rate: $R_{(y)}$ (%) | 9 | 20 | 44 | 47 |
| Evaluation for Criteria (z) | — | — | suitable | suitable |

TABLE 16-continued

| | Evaluation for Criteria | | | |
|---|---|---|---|---|
| Evaluation item | Comparative Example 6-1 | Comparative Example 6-2 | Example 6-1 | Example 6-2 |
| Disintegration | — | — | Not Occurred | Not Occurred |

TABLE 16-continued

| | Evaluation for Criteria | | | |
|---|---|---|---|---|
| Evaluation item | Comparative Example 6-1 | Comparative Example 6-2 | Example 6-1 | Example 6-2 |
| Overall evaluation | unsuitable | unsuitable | suitable | suitable |
| pH of Preparation | 6.8 | 11.2 | 11.4 | 11.3 |

—: Unmeasured

Test Example 7

Tablets shown in Table 17 and Table 18 were produced, and these tablets were evaluated.

<Preparation of Tablet>

The compositions of the tablets are shown in Table 17 and Table 18. Tablets having a tablet diameter of 8 mm were obtained according to the method as described in Test Example 1.

TABLE 17

| | Composition | |
|---|---|---|
| Component | Comparative Example 7-1 | Comparative Example 7-2 |
| Compound A | 0.4 mg | 0.4 mg |
| D-Mannitol<br>Mannit P (Mitsubishi Shoji Foodtech Co., Ltd.) | 103.15 mg | 93.65 mg |
| Water-Soluble Polymer: HPC<br>Klucel ® HXF | — | 19 mg |
| Functional Starch: Pregelatinized starch<br>SWELSTAR ® MX-1 | 76 mg | 76 mg |
| Alkaline Substance: Dried sodium carbonate<br>Dried sodium carbonate (Powdered)<br>(Takasugi Pharmaceutical Co., Ltd.) | 9.5 mg | — |
| Magnesium stearate<br>Magnesium stearate (Special grade)<br>(Taihei Chemical Industrial Co., Ltd.) | 0.95 mg | 0.95 mg |
| Total | 190 mg | 190 mg |

TABLE 18

| | Composition | | |
|---|---|---|---|
| Component | Example 7-1 | Example 7-2 | Example 7-3 |
| Compound A | 0.4 mg | 0.4 mg | 0.4 mg |
| D-Mannitol<br>Mannit P (Mitsubishi Shoji Foodtech Co., Ltd.) | 93.65 mg | 84.15 mg | 84.15 mg |
| Water-Soluble Polymer: HPMC<br>Metolose ® 90SH-4000SR | 9.5 mg | 19 mg | — |
| Water-Soluble Polymer: HPC<br>Klucel ® HXF | — | — | 19 mg |
| Functional Starch: Pregelatinized starch<br>SWELSTAR ® MX-1 | 76 mg | 76 mg | 76 mg |
| Alkaline Substance: Dried sodium carbonate<br>Dried sodium carbonate (Powdered)<br>(Takasugi Pharmaceutical Co., Ltd.) | 9.5 mg | 9.5 mg | 9.5 mg |
| Magnesium stearate<br>Magnesium stearate (Special grade)<br>(Taihei Chemical Industrial Co., Ltd.) | 0.95 mg | 0.95 mg | 0.95 mg |
| Total | 190 mg | 190 mg | 190 mg |

<Evaluation Method>

The tablets shown in Table 17 and Table 18 were evaluated in the same manner as in Test Example 2.

<Results>

The evaluation results of Comparative Example 7-1 and Comparative Example 7-2 are shown in Table 19, and the evaluation results of Example 7-1, Example 7-2 and Example 7-3 are shown in Table 20.

As shown in Table 19 and Table 20, Comparative Example 7-1 which contained the functional starch and the alkaline substance, but did not contain the water-soluble polymer did not satisfy the Criteria (y) and (z), while Example 7-1 which contained the water-soluble polymer (the amount of the water-soluble polymer:5 wt %), the functional starch and the alkaline substance, and Example 7-2 which contained the water-soluble polymer (the amount of the water-soluble polymer:10 wt %), the functional starch and the alkaline substance satisfied all the Criteria (x) to (z).

Further, Comparative Example 7-2 which contained the water-soluble polymer and the functional starch, but did not contain the alkaline substance did not satisfy the Criterion (y), while Example 7-3 which contained the water-soluble polymer, the functional starch and the alkaline substance satisfied all the Criteria (x) to (z).

TABLE 19

| Evaluation item | Comparative Example 7-1 | Comparative Example 7-2 |
|---|---|---|
| Test time: t (hours) | 6 | 18 |
| Dissolution rate: R (%) | 57 | 55 |
| Evaluation for Criteria (x) | suitable | suitable |
| Dissolution rate: $R_{(x)}$ (%) | 55 | 60 |
| Evaluation for Criteria (y) | unsuitable | unsuitable |
| Dissolution rate: $R_{(y)}$ (%) | 35 | 9 |
| Evaluation for Criteria (z) | unsuitable | — |
| Disintegration | Occurred | — |
| Overall evaluation | unsuitable | unsuitable |
| pH of Preparation | 11.4 | 7.4 |

—: Unmeasured

TABLE 20

| Evaluation item | Example 7-1 | Example 7-2 | Example 7-3 |
|---|---|---|---|
| Test time: t (hours) | 6 | 6 | 12 |
| Dissolution rate: R (%) | 56 | 51 | 53 |
| Evaluation for Criteria (x) | suitable | suitable | suitable |
| Dissolution rate: $R_{(x)}$ (%) | 55 | 55 | 60 |
| Evaluation for Criteria (y) | suitable | suitable | suitable |
| Dissolution rate: $R_{(y)}$ (%) | 48 | 46 | 41 |
| Evaluation for Criteria (z) | suitable | suitable | suitable |
| Disintegration | Not Occurred | Not Occurred | Not Occurred |
| Overall evaluation | suitable | suitable | suitable |
| pH of Preparation | 11.3 | 11.3 | 11.2 |

Test Example 8

Tablets shown in Table 21 and Table 22 were produced, and these tablets were evaluated.

<Preparation of Tablet>

The compositions of the tablets are shown in Table 21 and Table 22. Tablets having a tablet diameter of 8 mm were obtained according to the method as described in Test Example 1.

TABLE 21

| Component | Comparative Example 8-1 | Comparative Example 8-2 | Example 8-1 | Example 8-2 |
|---|---|---|---|---|
| Compound A | 0.4 mg | 0.4 mg | 0.4 mg | 0.4 mg |
| D-Mannitol Mannit P (Mitsubishi Shoji Foodtech Co., Ltd.) | 122.15 mg | 103.15 mg | 127.85 mg | 103.15 mg |
| Water-Soluble Polymer: HPMC Metolose ® 90SH-4000SR | 19 mg | 19 mg | 19 mg | 19 mg |
| Functional Starch: Pregelatinized starch SWELSTAR ® MX-1 | 38 mg | 38 mg | 38 mg | 38 mg |
| Alkaline Substance: Sodium hydrogen phosphate (Nacalai Tesque, Inc) | 9.5 mg | — | — | — |
| Alkaline Substance: Calcium carbonate (NACALAI TESQUE, INC) | — | 28.5 mg | — | — |
| Alkaline Substance: Calcium hydroxide (Nacalai Tesque, Inc) | — | — | 3.8 mg | — |
| Alkaline Substance: Magnesium hydroxide (Tomita Pharmaceutical Co., Ltd.) | — | — | — | 28.5 mg |
| Magnesium stearate Magnesium stearate (Special grade) (Taihei Chemical Industrial Co., Ltd.) | 0.95 mg | 0.95 mg | 0.95 mg | 0.95 mg |
| Total | 190 mg | 190 mg | 190 mg | 190 mg |

TABLE 22

| Component | Example 8-3 | Example 8-4 | Example 8-5 | Example 8-6 |
|---|---|---|---|---|
| Compound A | 0.4 mg | 0.4 mg | 0.4 mg | 0.4 mg |
| D-Mannitol Mannit P (Mitsubishi Shoji Foodtech Co., Ltd.) | 129.75 mg | 127.85 mg | 122.15 mg | 116.45 mg |
| Water-Soluble Polymer: HPMC Metolose ® 90SH-4000SR | 19 mg | 19 mg | 19 mg | 19 mg |
| Functional Starch: Pregelatinized starch SWELSTAR ® MX-1 | 38 mg | 38 mg | 38 mg | 38 mg |
| Alkaline Substance: Dried sodium carbonate Dried sodium carbonate (Powdered) (Takasugi Pharmaceutical Co., Ltd.) | 1.9 mg | 3.8 mg | 9.5 mg | 15.2 mg |
| Magnesium stearate Magnesium stearate (Special grade) (Taihei Chemical Industrial Co., Ltd.) | 0.95 mg | 0.95 mg | 0.95 mg | 0.95 mg |
| Total | 190 mg | 190 mg | 190 mg | 190 mg |

<Evaluation Method>

The tablets shown in Table 21 and Table 22 were evaluated in the same manner as in Test Example 2.

<Results>

The evaluation results of Comparative Example 8-1, Comparative Example 8-2, Example 8-1, and Example 8-2 are shown in Table 23, and the evaluation results of Example 8-3, Example 8-4, Example 8-5, and Example 8-6 are shown in Table 24.

As shown in Table 23 and Table 24, the tablets containing disodium hydrogen phosphate or calcium carbonate as the alkaline substance had a pH less than 10.0, and did not satisfy the Criterion (y) (see the evaluation results of Comparative Examples 8-1 and 8-2 in Table 23), while the tablets containing calcium hydroxide, magnesium hydroxide, or dried sodium carbonate as the alkaline substance had a pH of 10.0 or more, and satisfied all the Criteria (x) to (z) (see the evaluation results of Example 8-1 and Example 8-2 in Table 23 and the evaluation results of Example 8-3 to Example 8-6 in Table 24).

TABLE 23

| Evaluation item | Comparative Example 8-1 | Comparative Example 8-2 | Example 8-1 | Example 8-2 |
|---|---|---|---|---|
| Test time: t (hours) | 4 | 8 | 6 | 4 |
| Dissolution rate: R (%) | 48 | 54 | 52 | 48 |
| Evaluation for criteria (x) | suitable | suitable | suitable | suitable |
| Dissolution rate: $R_{(x)}$ (%) | 51 | 56 | 56 | 51 |
| Evaluation for Criteria (y) | unsuitable | unsuitable | suitable | suitable |
| Dissolution rate: $R_{(y)}$ (%) | 25 | 16 | 53 | 37 |
| Evaluation for Criteria (z) | suitable | unsuitable | suitable | suitable |
| Disintegration | Not Occurred | Occurred | Not Occurred | Not Occurred |
| Overall evaluation | unsuitable | unsuitable | suitable | suitable |
| pH of Preparation | 9.2 | 8.8 | 11.8 | 10.1 |

TABLE 24

| Evaluation item | Example 8-3 | Example 8-4 | Example 8-5 | Example 8-6 |
|---|---|---|---|---|
| Test time: t (hours) | 4 | 4 | 4 | 4 |
| Dissolution rate: R (%) | 49 | 50 | 51 | 51 |
| Evaluation for criteria (x) | suitable | suitable | suitable | suitable |
| Dissolution rate: $R_{(x)}$ (%) | 59 | 60 | 62 | 56 |
| Evaluation for criteria (y) | suitable | suitable | suitable | suitable |
| Dissolution rate: $R_{(y)}$ (%) | 39 | 45 | 46 | 44 |
| Evaluation for Criteria (z) | suitable | suitable | suitable | suitable |
| Disintegration | Not Occurred | Not Occurred | Not Occurred | Not Occurred |
| Overall evaluation | suitable | suitable | suitable | suitable |
| pH of Preparation | 10.9 | 11.2 | 11.4 | 11.5 |

Test Example 9

Tablets shown in Table 25 were produced, and these tablets were evaluated.

<Preparation of Film-Coated Tablet>

Example 9-1

The composition of the tablets is shown in Table 25. Compound A, lactose hydrate, crystalline cellulose, HPMC, pregelatinized starch, dried sodium carbonate, and magnesium stearate were mixed in a mortar, and the resulting mixed powder was compressed at 1000 kgf using AUTOGRAPH AG-50kNXD (manufactured by Shimadzu Corporation) to obtain a tablet having a tablet diameter of 8 mm. The obtained tablets were placed in a tablet coating machine (DRC-200, manufactured by Powrex Corporation), and a coating liquid (prepared by dispersing a mixture of lactose hydrate, HPMC, titanium oxide and macrogol in water at the 20 wt % of solid fraction) was sprayed on the tablets to obtain film-coated tablets. Imitation tablets were appropriately used so that the charged amount in the tablet coating machine made a proper amount for coating.

TABLE 25

| Component | Example 9-1 |
|---|---|
| Compound A | 0.4 mg |
| Lactose hydrate<br>Pharmatose ® 200M | 108.2 mg |
| Crystalline cellulose<br>Ceolus ® PH101 | 19 mg |
| Water-Soluble Polymer: HPMC<br>Metolose ® 90SH-100000SR | 17 mg |
| Functional Starch: Pregelatinized starch<br>SWELSTAR ® MX-1 | 34 mg |
| Alkaline Substance: Dried sodium carbonate<br>Dried sodium carbonate (Powdered)<br>(Takasugi Pharmaceutical Co., Ltd.) | 9.5 mg |
| Magnesium stearate<br>Magnesium stearate (Special grade)<br>(Taihei Chemical Industrial Co., Ltd.) | 1.9 mg |
| Mixture of lactose hydrate, HPMC, titanium oxide and macrogol Opadry ® OY-L-28900 | 15 mg |
| Total | 205 mg |

Example 9-2

The composition of the tablets is shown in Table 26. Compound A, crystalline cellulose, HPMC (Metolose® 90SH-100000SR), pregelatinized starch, dried sodium carbonate, and magnesium stearate were mixed in a mortar, and the resulting mixed powder was compressed at 800 kgf using AUTOGRAPH AG-50kNXD (manufactured by Shimadzu Corporation) to obtain a tablet having a tablet diameter of 6.5 mm. The obtained tablets were placed in a tablet coating machine (DRC-200, manufactured by Powrex Corporation), and a coating liquid (prepared by dispersing HPMC)(TC-5R°, propylene glycol and titanium oxide in water at the 10 wt % of solid fraction) was sprayed on the tablets to obtain film-coated tablets. Imitation tablets were appropriately used so that the charged amount in the tablet coating machine made a proper amount for coating.

TABLE 26

| Component | Example 9-2 |
|---|---|
| Compound A | 0.4 mg |
| Crystalline cellulose<br>Ceolus ® PH101 | 8.6 mg |
| Water-Soluble Polymer: HPMC<br>Metolose ® 90SH-100000SR | 75 mg |
| Functional Starch: Pregelatinized starch<br>SWELSTAR ® MX-1 | 20 mg |
| Alkaline Substance: Dried sodium carbonate<br>Dried sodium carbonate (Powdered)<br>(Takasugi Pharmaceutical Co., Ltd.) | 5 mg |
| Magnesium stearate<br>Magnesium stearate (Special grade)<br>(Taihei Chemical Industrial Co., Ltd.) | 1 mg |
| HPMC<br>TC-5R ® | 3.8 mg |
| Propylene glycol<br>Propylene glycol (Asahi glass, INC) | 0.6 mg |
| Titanium oxide<br>Tipaque ® A-100 | 0.6 mg |
| Total | 115 mg |

<Evaluation Method>

The tablets shown in Table 25 and Table 26 were evaluated in the same manner as in Test Example 2.

<Results>

The evaluation results of Example 9-1 and Example 9-2 are shown in Table 27.

The film-coated tablets which contained the water-soluble polymer, the functional starch, and the alkaline substance satisfied all the Criteria (x) to (z).

TABLE 27

| Evaluation item | Example 9-1 | Example 9-2 |
|---|---|---|
| Test time: t (hours) | 4 | 12 |
| Dissolution rate: R (%) | 44 | 48 |
| Evaluation for Criteria (x) | suitable | suitable |
| Dissolution rate: $R_{(x)}$ (%) | 54 | 60 |
| Evaluation for Criteria (y) | suitable | suitable |
| Dissolution rate: $R_{(y)}$ (%) | 40 | 39 |
| Evaluation for Criteria (z) | suitable | suitable |
| Disintegration | Not Occurred | Not Occurred |
| Overall evaluation | suitable | suitable |
| pH of Preparation | 11.2 | 11.3 |

Test Example 10

Tablets shown in Table 28 were produced, and these tablets were evaluated.

<Preparation of Tablet>

The compositions of the tablets are shown in Table 28. The components were weighed and mixed in a mortar, and the resulting mixed powder was compressed using AUTOGRAPH AG-50kNXD (manufactured by Shimadzu Corporation). In Example 10-1, Example 10-2, and Example 10-4, the tablets having a tablet diameter of 8 mm were obtained by performing the compression at 1000 kgf. In Example 10-3, the tablet having a tablet diameter of 9.5 mm was obtained by performing the compression at 1200 kgf.

TABLE 28

| Component | Example 10-1 | Example 10-2 | Example 10-3 | Example 10-4 |
|---|---|---|---|---|
| Compound A | 0.4 mg | 0.8 mg | 1.2 mg | 2.0 mg |
| D-Mannitol Mannit P (Mitsubishi Shoji Foodtech Co., Ltd.) | 122.15 mg | — | — | — |
| Lactose hydrate Pharmatose ® 200M | — | 117.2 mg | 175.8 mg | 64 mg |
| Water-Soluble Polymer: HPMC Metolose ® 90SH-100000SR | 19 mg | — | — | — |
| Water-Soluble Polymer: HPMC Metolose ® 90SH-4000SR | — | 20 mg | 30 mg | — |
| Water-Soluble Polymer: HPMC Metolose ® 90SH-100SR | — | — | — | 40 mg |
| Functional Starch: Pregelatinized starch SWELSTAR ® MX-1 | 38 mg | 50 mg | 75 mg | 80 mg |
| Alkaline Substance: Dried sodium carbonate Dried sodium carbonate (Powdered) (Takasugi Pharmaceutical Co., Ltd.) | 9.5 mg | 10 mg | 15 mg | 12 mg |
| Magnesium stearate Magnesium stearate (Special grade) (Taihei Chemical Industrial Co., Ltd.) | 0.95 mg | — | — | 2 mg |
| Sodium Stearyl Fumarate PRUV ® | — | 2 mg | 3 mg | — |
| Total | 190 mg | 200 mg | 300 mg | 200 mg |

<Evaluation Method>

The tablets shown in Table 28 were evaluated in the same manner as in Test Example 2.

<Results>

The evaluation results of Example 10-1, Example 10-2, Example 10-3, and Example 10-4 are shown in Table 29.

These Examples, in which the water-soluble polymer, the functional starch and the alkaline substance were contained, satisfied all the Criteria (x) to (z).

TABLE 29

| Evaluation item | Example 10-1 | Example 10-2 | Example 10-3 | Example 10-4 |
|---|---|---|---|---|
| Test time: t (hours) | 4 | 6 | 6 | 8 |
| Dissolution rate: R (%) | 45 | 55 | 48 | 52 |
| Evaluation for criteria (x) | suitable | suitable | suitable | suitable |
| Dissolution rate: $R_{(x)}$ (%) | 52 | 62 | 52 | 56 |
| Evaluation for criteria (y) | suitable | suitable | suitable | suitable |
| Dissolution rate: $R_{(y)}$ (%) | 40 | 45 | 41 | 40 |
| Evaluation for criteria (z) | suitable | suitable | suitable | suitable |
| Disintegration | Not Occurred | Not Occurred | Not Occurred | Not Occurred |
| Comprehensive evaluation | suitable | suitable | suitable | suitable |
| pH of Preparation | 11.3 | 11.3 | 11.3 | 11.4 |

As shown in the Test Examples provided above, it is apparent that the controlled-release preparation containing Compound A as an active ingredient, in combination with a water-soluble polymer, a functional starch and an alkaline substance, is less affected by the property of the test solution (pH) and the stirring intensity (paddle rotation speed).

INDUSTRIAL APPLICABILITY

Thus, the controlled-release preparation of the present invention is useful as a sustained-release preparation which is required to maintain the release of the active ingredient at a constant rate for a long period of time.

The invention claimed is:

1. A controlled-release preparation, characterized by comprising 2-{4-[N-(5,6-diphenylpyrazin-2-yl)-N-isopropylamino]butyloxy}-N-(methylsulfonyl)acetamide, a water-soluble polymer, a functional starch, and an alkaline substance, and having a pH of 10 or more.

2. The controlled-release preparation according to claim 1, wherein the water-soluble polymer is a polymer whose aqueous solution at a concentration of 10 wt % or less has a viscosity of 1000 mPa·s or more at 25° C.

3. The controlled-release preparation according to claim 1, wherein the water-soluble polymer is at least one selected from the group consisting of hypromellose, hydroxypropylcellulose, and polyvinyl alcohol.

4. The controlled-release preparation according to claim 1, wherein the amount of the water-soluble polymer contained in the preparation is within the range from 5 wt % to 70 wt % with respect to the total weight of the preparation.

5. The controlled-release preparation according to claim 1, wherein the functional starch is (a) or (b):
   (a) a starch whose aqueous suspension at 7 wt % has a viscosity within the range from 100 mPa·s to 1500 mPa·s at 25° C.; or
   (b) a starch which does not disintegrate even after 1 hour in a disintegration test using an auxiliary disk according to the Japanese Pharmacopoeia 17$^{th}$ edition when the starch is subjected to compression molding.

6. The controlled-release preparation according to claim 1, wherein the amount of the functional starch contained in the preparation is within the range from 15 wt % to 70 wt % with respect to the total weight of the preparation.

7. The controlled-release preparation according to claim 1, wherein the total amount of the water-soluble polymer and the functional starch contained in the preparation is within the range from 25 wt % to 85 wt % with respect to the total weight of the preparation.

8. The controlled-release preparation according to claim 1, wherein the alkaline substance is an alkaline substance whose aqueous solution at 0.1 wt % has a pH of 10 or more.

9. The controlled-release preparation according to claim 1, wherein the amount of the alkaline substance contained in the preparation is within the range from 1 wt % to 15 wt % with respect to the total weight of the preparation.

10. The controlled-release preparation according to claim 1, characterized in that the preparation satisfies all the following Criteria (x) to (z):
Criterion (x): under the conditions of a dissolution test in which 900 mL of a test solution at pH 6.8 is used and a paddle rotation speed is set to 200 rpm, a dissolution rate ($R_{(x)}$) at the time t is within the range of R±15%;
Criterion (y): under the conditions of a dissolution test in which 900 mL of a test solution at pH 5.0 is used and a paddle rotation speed is set to 50 rpm, a dissolution rate ($R_{(y)}$) at the time t is within a range of R±15%; and
Criterion (z): under the conditions of a dissolution test in which 500 mL of a test solution at pH 1.2 is used and a paddle rotation speed is set to 200 rpm, the preparation does not disintegrate at the time t;
wherein t is the time to release 40 to 60% of 2-{4-[N-(5,6-diphenylpyrazin-2-yl)-N-isopropylamino]butyloxy}-N-(methylsulfonyl)acetamide in the preparation and R is the dissolution rate at the time t, under the conditions of a dissolution test in which 900 mL of a test solution at pH 6.8 is used and the paddle rotation speed is set to 50 rpm.

11. The controlled-release preparation according to claim 10, wherein the water-soluble polymer is a polymer whose aqueous solution at a concentration of 10 wt % or less has a viscosity of 1000 mPa·s or more at 25° C.

12. The controlled-release preparation according to claim 11, wherein the water-soluble polymer is at least one selected from the group consisting of hypromellose, hydroxypropylcellulose, and polyvinyl alcohol.

13. The controlled-release preparation according to claim 12, wherein the functional starch is (a) or (b):
(a) a starch whose aqueous suspension at 7 wt % has a viscosity within the range from 100 mPa·s to 1500 mPa·s at 25° C.; or
(b) a starch which does not disintegrate even after 1 hour in a disintegration test using an auxiliary disk according to the Japanese Pharmacopoeia 17$^{th}$ edition when the starch is subjected to compression molding.

14. The controlled-release preparation according to claim 13, wherein the alkaline substance is an alkaline substance whose aqueous solution at 0.1 wt % has a pH of 10 or more.

15. The controlled-release preparation according to claim 1, wherein the controlled-release preparation is a sustained-release preparation.

16. The controlled-release preparation according to claim 1, wherein the controlled-release preparation is a tablet or a capsule.

17. The controlled-release preparation according to claim 1, for use in the treatment of symptoms associated with diabetic neuropathy, diabetic gangrene, a peripheral circulatory disturbance, chronic arterial occlusion, intermittent claudication, scleroderma, thrombosis, pulmonary hypertension, myocardial infarction, angina pectoris, glomerulonephritis, diabetic nephropathy, chronic renal failure, bronchial asthma, interstitial pneumonia, pulmonary fibrosis, a chronic obstructive pulmonary disease, tubulointerstitial nephritis, an inflammatory bowel disease, or spinal canal stenosis.

18. A controlled-release preparation comprising 2-{4-[N-(5,6-diphenylpyrazin-2-yl)-N-isopropylamino]butyloxy}-N-(methylsulfonyl)acetamide as an active ingredient characterized in that the preparation satisfies all the following Criteria (x) to (z):
Criterion (x): under the conditions of a dissolution test in which 900 mL of a test solution at pH 6.8 is used and a paddle rotation speed is set to 200 rpm, a dissolution rate (R(x)) at the time t is within the range of R±15%;
Criterion (y): under the conditions of a dissolution test in which 900 mL of a test solution at pH 5.0 is used and a paddle rotation speed is set to 50 rpm, a dissolution rate (R(y)) at the time t is within a range of R±15%; and
Criterion (z): under the conditions of a dissolution test in which 500 mL of a test solution at pH 1.2 is used and a paddle rotation speed is set to 200 rpm, the preparation does not disintegrate at the time t;
wherein t is the time to release 40 to 60% of 2-{4-[N-(5,6-diphenylpyrazin-2-yl)-N-isopropylamino]butyloxy}-N-(methylsulfonyl)acetamide in the preparation and R is the dissolution rate at the time t, under the conditions of a dissolution test in which 900 mL of a test solution at pH 6.8 is used and the paddle rotation speed is set to 50 rpm.

19. A method for the treatment or prevention of a disease comprising administering a therapeutically effective amount of a controlled-release preparation to a patient in need thereof, wherein the preparation comprises 2-{4-[N-(5,6-diphenylpyrazin-2-yl)-N-isopropylamino]butyloxy}-N-(methylsulfonyl)acetamide, a water-soluble polymer, a functional starch and an alkaline substance, and has a pH of 10 or more.

* * * * *